(12) United States Patent
Le et al.

(10) Patent No.: US 7,250,479 B2
(45) Date of Patent: Jul. 31, 2007

(54) POLYMERIZATION WITH LIVING CHARACTERISTICS

(75) Inventors: Tam Phuong Le, Victoria (AU); Graeme Moad, Victoria (AU); Ezio Rizzardo, Victoria (AU); San Hoa Thang, Victoria (AU)

(73) Assignees: E. I. du Pont de Nemours and Company, Wilmington, DE (US); Commonwealth Scientific and Industrial Research Organization, Victoria (AU)

( * ) Notice: Subject to any disclaimer, the term of this patent is extended or adjusted under 35 U.S.C. 154(b) by 331 days.

(21) Appl. No.: 10/784,425

(22) Filed: Feb. 23, 2004

(65) Prior Publication Data

US 2004/0171777 A1 Sep. 2, 2004

Related U.S. Application Data

(62) Division of application No. 09/762,833, filed as application No. PCT/US97/12540 on Jul. 3, 1997, now abandoned.

(30) Foreign Application Priority Data

Jul. 10, 1996 (AU) .................................... PO0933
Jul. 10, 1996 (AU) .................................... PO1109

(51) Int. Cl.
*C08F 2/00* (2006.01)
(52) U.S. Cl. .................. 526/193; 526/213; 526/215; 526/216; 526/219; 526/220; 526/222
(58) Field of Classification Search ................ 526/193, 526/213, 215, 216, 219, 220, 222
See application file for complete search history.

(56) References Cited

U.S. PATENT DOCUMENTS 2,396,997 A 3/1946 Fryling

FOREIGN PATENT DOCUMENTS

| EP | 0348166 A | 12/1989 |
| JP | 04198303 | 7/1992 |
| WO | WO 92/13903 A | 8/1992 |
| WO | WO 93/22351 | 11/1993 |
| WO | WO 93/22355 | 11/1993 |
| WO | WO 96/15157 | 5/1996 |

OTHER PUBLICATIONS

Quirk & Lee (Polymer International) 27, 359 (1992).
Moad et al., Comprehensive Polymer Science, Pergamon, London, Wvol. 3, p. 141 (1989).
Greszta et al., Macromolecules 27, 638 (1994).
Rizzardo et al., Macromol Symp. 98, 101 (1995).
Cacioli et al., Copolymerization of ω-Unsaturated Oligo(Methyl) Methacrylate): New Macromonomers, J. Macromol Sci-Chem A23, 839 (1986).
Moad & Solomon, The Chemistry of Free Radical Polymerization, Pergamon, London 1995, pp. 53-95.
Greenley, Polymer Handbook 3rd Edition, Wiley, NY 1989 p. 11/53.
Muller et al., Macromolecules 1995, 28, 4326.
Jensen et al., Acta Chem. Scand., 15, 1087-1096 (1961).
O'Driscoll et al., Eur. Polym. J. 25(7/8) 629 (1989).
Szwarc, Living Polymers and Mechanisms of Anionic Polymerization, 1983.
Moebius et al., Beschleuniger fur Cyanacrylatklebstoffe, Plaste Und Kautschuk, vol. 39, No. 4, 1994, pp. 122-123—XP002046219.
Delfanne et al., Polythioamide and Poly(1,3,4-thiadiazole) Synthesis from Dimethyl Tetrathioterephthalate Macromolecules, vol. 22, 1989, pp. 2589-2592—XP002046220.
Chemical Abstracts 116: 130 869—XP002046221.

*Primary Examiner*—Bernard Lipman
(74) *Attorney, Agent, or Firm*—Sudhir G. Deshmukh

(57) ABSTRACT

This invention concerns a free radical polymerization process, selected chain transfer agents employed in the process and polymers made thereby, in which the process comprises preparing polymer of general Formula (A) and Formula (B) comprising contacting: (i) a monomer selected from the group consisting of vinyl monomers (of structure $CH_2=CUV$), maleic anhydride, N-alkylmaleimide, N-arylmaleimide, dialkyl fumarate and cyclopolymerizable monomers; (ii) a thiocarbonylthio compound selected from Formula (C) and Formula (D) having a chain transfer constant greater than about 0.1; and (iii) free radicals produced from a free radical source; the polymer of Formula (A) being made by contacting (i), (ii) C and (iii) and that of Formula (B) by contacting (i), (ii) D, and (iii); and (iv) controlling the polydispersity of the polymer being formed by varying the ratio of the number of molecules of (ii) to the number of molecules of (iii); wherein Q, R, U, V, Z, Z', m, p and q are as defined in the text (A)

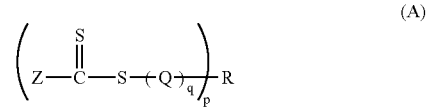

(B)

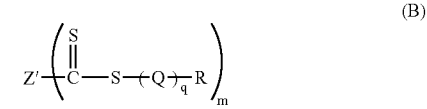

(C)

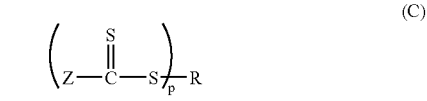

(D)

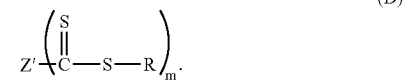

45 Claims, No Drawings

POLYMERIZATION WITH LIVING CHARACTERISTICS

This application is a divisional of application Ser. No. 09/762,833 filed on Jan. 30, 2001 now abandoned, which is a § 371 of PCT/US97/12540 filed on Jul. 3, 1997, which takes priority from Australian provisional applications PO 1109 filed on Jul. 18, 1996 and PO 0933 filed on Jul. 10, 1996.

BACKGROUND OF THE INVENTION

This invention relates to a free radical polymerization process with characteristics of a living polymerization system in that it is capable of producing polymers of predetermined molecular weight with narrow molecular weight distribution (low polydispersity), and, by successively adding different monomers, can be used to make block polymers. The process can be used to produce polymers of more complex architecture, including variously branched homo- and copolymers. The use of certain reagents in this process and the polymers produced thereby are also claimed. Novel chain transfer agents for use in the process are also claimed.

There is increasing interest in methods for producing a variety of polymers with control of the major variables affecting polymer properties. Living polymerizations provide the maximum degree of control for the synthesis of polymers with predictable well defined structures. The characteristics of a living polymerization are discussed by Quirk and Lee (*Polymer International* 27, 359 (1992)) who give the following experimentally observable criteria:

"1. Polymerization proceeds until all of the monomer has been consumed. Further addition of monomer results in continued polymerization.
2. The number average molecular weight (or the number average degree of polymerization) is a linear function of conversion.
3. The number of polymer molecules (and active centers) is a constant which is sensibly independent of conversion.
4. The molecular weight can be controlled by the stoichiometry of the reaction.
5. Narrow molecular weight distribution polymers are produced.
6. Block copolymers can be prepared by sequential monomer addition.
7. Chain end-functionalized polymers can be prepared in quantitative yield."

Living polymerization processes can be used to produce polymers of narrow molecular weight distribution containing one or more monomer sequences whose length and composition are controlled by the stoichiometry of the reaction and the degree of conversion. Homopolymers, random copolymers or block polymers can be produced with a high degree of control and with low polydispersity. Swarc (*Adv. Polym. Sci.* 49, 1 (1983)) stated that living polymerization to give polymers of narrow molecular weight distribution requires the absence of chain transfer and termination reactions, the elementary reactions being only initiation and propagation, which take place uniformly with respect to all growing polymer chains. Later Inoue and Aida in an article on living polymer systems (*Encyclopedia of Polymer Science and Engineering*, Supplement Volume, Wiley Interscience New York 1989) stated "If chain transfer and terminating agents are present in the polymerization system the living character of the polymerization is lost, and the formation of polymer with narrow molecular weight distribution does not result."

However, it has been shown that if the chain transfer process is reversible then polymerization can still possess most of the characteristics of living polymerization. A variety of terms have been used to describe polymerizations believed to involve this mechanism including "immortal polymerization", "equilibration polymerization", "polymerization with degenerative chain transfer" and "living polymerization with reversible chain transfer". Quirk and Lee (*Polymer International* 27, 359 (1992)), who recommend the last terminology, point out that the Criteria 3 and 4 mentioned above need to be modified when describing these polymerizations to encompass the fact that the total number of polymer molecules is determined by the total number of moles of transfer agent plus the number of moles of initiator.

Block copolymer syntheses by free radical polymerization in the presence of certain dithiocarbamate or xanthate derivatives as initiator-transfer agents-chain terminators (iniferters) have been described. In these examples the dithiocarbamate or xanthate derivative is used as a photochemical initiator. For a discussion of this chemistry see recent reviews [Moad et al. in *Comprehensive Polymer Science*; Pergamon: London, vol 3, p 141 (1989)]. The dithiocarbamates (for example, benzyl dithiocarbamate) have very low transfer constants (<<0.1) and are ineffective in the context of the current invention. Greszta et al. (*Macromolecules*, 27, 638 (1994)) have described the application of chain transfer chemistry in living radical polymerization and have proposed and rejected the use of dithiocarbamates in this context because of the low transfer constant and the problem of side reactions. JP 04198303 A2 discloses polymerization in the presence of triarylmethyl dithiocarboxylates of the following structure

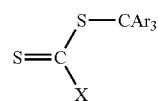

X = alkyl or aryl as initiators of polymerization to yield block polymers which may have low polydispersity (all examples have $M_w/M_n^3$ 1.4). These compounds have a very weak carbon-sulfur bond that cleaves under polymerization conditions to give a stable triarylmethyl radical and a thiocarbonylthiyl radical. The product triarylmethyl radical is known to be a poor initiator of radical polymerization. They are thus ineffective in the context of this invention.

Rizzardo et al. (*Macromol. Symp.* 98, 101 (1995)) review polymerization in the presence of addition-fragmentation chain transfer agents but do not mention the possibility of low polydispersity products.

Polymers or oligomers of the following structure are known as macromonomers.

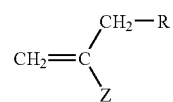

These macromonomers which are addition-fragmentation chain transfer agents are disclosed in *J Macromol. Sci.—*

*Chem.* A23, 839 (1986) and International Patent publications WO 93/22351 and WO 93/22355. Free radical polymerization with living characteristics utilizing these macromonomers as chain transfer agents is disclosed in International Patent Application PCT/US95/14428. The process of this invention has the advantages of compatibility with a wide range of monomers and reaction conditions and will give good control over molecular weight, molecular weight distribution, i.e., polydispersity, and polymer architecture.

SUMMARY OF THE INVENTION

This invention concerns a process for the synthesis of polymers of the general Formula:

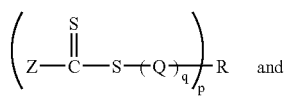 Formula A and

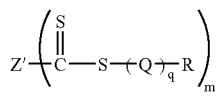 Formula B comprising contacting:
(i) a monomer (means one or more) selected from the group consisting of vinyl monomers (of structure $CH_2=CUV$), maleic anhydride, N-alkylmaleimide, N-arylmaleimide, dialkyl fumarate and cyclopolymerizable monomers;
(ii) a thiocarbonylthio compound selected from:

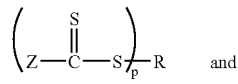 Formula C and

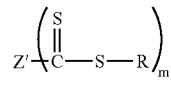 Formula D having a chain transfer constant greater than about 0.1; and
(iii) free radicals produced from a free radical source; and
controlling the polydispersity of the polymer being formed by varying the ratio of the number of molecules of (ii) to the number of molecules of (iii);
the polymer of Formula A being made by contacting (i), (ii) C and (iii) and the polymer of Formula B being made by contacting (i), (ii) D and (iii);

wherein:
Z is selected from the group consisting of hydrogen, chlorine, optionally substituted alkyl, optionally substituted aryl, optionally substituted heterocyclyl, optionally substituted alkylthio, optionally substituted alkoxycarbonyl, optionally substituted aryloxycarbonyl (—COOR"), carboxy (—COOH), optionally substituted acyloxy (—$O_2CR$"), optionally substituted carbamoyl (—$CONR"_2$), cyano (—CN), dialkyl- or diarylphosphonato [—P(=O)(OR")$_2$], dialkyl- or diarylphosphinato [—P(=O)R"$_2$], and a polymer chain formed by any mechanism;
Z' is a m-valent moiety derived from a member of the group consisting of optionally substituted alkyl, optionally substituted aryl and a polymer chain; where the connecting moieties are selected from the group that consists of aliphatic carbon, aromatic carbon, and sulfur;
Q is selected from the group consisting of repeating unit

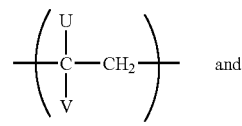 and and repeating units from maleic anhydride, N-alkylmaleimide, N-arylmaleimide, dialkyl fumarate and cyclopolymerizable monomers;
U is selected from the group consisting of hydrogen, halogen, optionally substituted $C_1$-$C_4$ alkyl wherein the substituents are independently selected from the group that consists of hydroxy, alkoxy, aryloxy (OR"), carboxy, acyloxy, aroyloxy ($O_2CR$"), alkoxy-carbonyl and aryloxy-carbonyl ($CO_2R$");
V is selected from the group consisting of hydrogen, R", $CO_2H$, $CO_2R$", COR", CN, $CONH_2$, CONHR", $CONR"_2$, $O_2CR$", OR" and halogen;
R is selected from the group consisting of optionally substituted alkyl; an optionally substituted saturated, unsaturated or aromatic carbocyclic or heterocyclic ring; optionally substituted alkylthio; optionally substituted alkoxy; optionally substituted dialkylamino; an organometallic species; and a polymer chain prepared by any polymerization mechanism; in compounds C and D, R. is a free-radical leaving group that initiates free radical polymerization;
R" is selected from the group consisting of optionally substituted $C_1$-$C_{18}$ alkyl $C_2$-$C_{18}$ alkenyl, aryl, heterocyclyl, aralkyl, alkaryl wherein the substituents are independently selected from the group that consists of epoxy, hydroxy, alkoxy, acyl, acyloxy, carboxy and carboxylates, sulfonic acid and sulfonates, alkoxy- or aryloxy-carbonyl, isocyanato, cyano, silyl, halo, and dialkylamino;
q is 1 or an integer greater than 1;
p is 1 or an integer greater than 1; when $p \geq 2$, then R=R';
m is an integer $\geq 2$; and
R' is a p-valent moiety derived from a member of the group consisting of optionally substituted alkyl optionally substituted aryl and a polymer chain; where the connecting moieties are selected from the group consisting of aliphatic carbon, aromatic carbon, silicon, and sulfur; in compounds C, R'. is a free radical leaving group that initiates free radical polymerization.

Preferred is a process as described for controlling polydispersity by varying the ratio of the number of molecules of (ii) to (iii) as follows:
(a) lower polydispersity by increasing the ratio of (ii) to (iii); and
(b) increase polydispersity by decreasing the ratio of (ii) to (iii).

Most preferred is the process in which the ratio of (ii) to (iii) is increased to obtain a polymer having a polydispersity below about 1.5.

The monomer moieties and value of q in the monomer repeating unit(s) derived from those in (i) are selected so that:

when q≧1 and Q is a single monomer species, then the polymer is homopolymer;

when q≧2 and Q is selected from 2 or more different monomer species in irregular sequence then the polymer is copolymer; and when q≧2 and Q is selected from 2 or more different monomer species in which each different monomer or group of monomers appears in a discrete sequence then the polymer is block copolymer.

The invention also concerns chain transfer agents designated hereafter as (5), (6), (7), (8), (9), (10), (11), (14), (15), (17), (18), (19), (22), (23), (24), (25), (28) and (29). The invention also concerns polymers of Formulae A and B with substituents as defined above. In polymers of Formulae A and B, R. and R'. are derived from free radical leaving group(s) that initiate free radical polymerization, $R\text{-}(Q)_q$. and $R'\text{-}(Q)_q$. being the free radical leaving group(s) that initiate free radical polymerization. Preferred polymers are random, block (most preferred), graft, star and gradient copolymers; most especially those having chain-end functionality. Compounds of Formulae C and D can be used to produce branched, homo- or copolymers with the number of arms being less than or equal to p in C and m in D.

Definitions

By polymer chains formed by any mechanism (in Z or R), is meant: condensation polymers such as polyesters (for example, polycaprolactone, polyethylene terephthalate), polycarbonates, poly(alkylene oxide)s [for example, poly(ethylene oxide), poly(tetramethylene oxide)], nylons, polyurethanes and chain polymers such as poly(meth)acrylates and polystyrenics.

Cyclopolymerizable monomers are compounds which contain two or more unsaturated linkages suitably disposed to allow propagation by a sequence of intramolecular and intermolecular addition steps leading the the incorporation of cyclic units into the polymer backbone. Most compounds of this class are 1,6-dienes such as—diallylammonium salts (e.g., diallyldimethylammonium chloride), substituted 1,6-heptadienes (e.g., 6-dicyano-1,6-heptadiene, 2,4,4,6-tetrakis(ethoxycarbonyl)-1,6-heptadiene) and monomers of the following generic structure

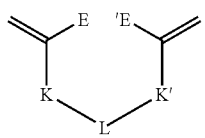

where substituents K, K', L, E, E' are chosen such that the monomer undergoes cyclopolymerization. For example:

E, E' are independently selected from the group consisting of H, $CH_3$, CN, $CO_2Alkyl$, Ph; K, K' are selected from the group consisting of $CH_2$, C=O, $Si(CH_3)_2$, O; L is selected from the group consisting of $C(E)_2$, O, $N(Alkyl)_2$ salts, $P(Alkyl)_2$ salts, P(O)Alkyl. For a further list of monomers see Moad and Solomon "The Chemistry of Free Radical Polymerization", Pergamon, London, 1995, pp 162-170.

By organometallic species is meant a moiety containing one or more metal atoms from Groups III and IV of the Periodic Table and transition elements and organic ligands, preferably species such as $Si(X)_3$, $Ge(X)_3$ and $Sn(X)_3$ which can be good radical leaving groups and initiate polymerization.

DETAILS OF THE INVENTION

We have now discovered that free radical polymerizations when cared out in the presence of certain chain transfer agents of the following structure:

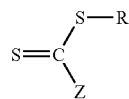

have living characteristics and provide polymers of controlled molecular weight and low polydispersity. Chain transfer agents applicable in this invention are designated as CTAs hereinafter.

While not wishing to be limited to any particular mechanism, it is believed that the mechanism of the process is as summarized in Scheme 1 below. Propagating radicals $P_n$. are produced by radical polymerization. These can react reversibly with the chain transfer agent RA to form an intermediate radical $P_nA(.)R$ which fragments to give a radical R. (which adds monomer to reinitiate polymerization) and a new transfer agent $P_nA$. This new transfer agent $P_nA$ has similar characteristics to the original transfer agent RA in that it reacts with another propagating radical $P_m$. to form an intermediate radical $P_nA(.)P_m$ which fragments to regenerate $P_n$. and form a new transfer agent $P_mA$ which has similar characteristics to RA. This process provides a mechanism for chain equilibration and accounts for the polymerization having living characteristics.

Scheme 1:

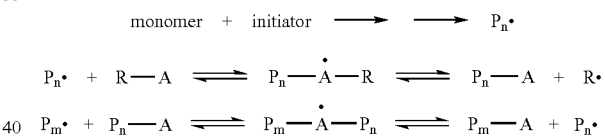

$P_n$. and $P_m$. are propagating radicals of chain length n and m respectively.

R. is a chain transfer agent derived radical which can initiate polymerization to produce a new propagating radical.

RA, $P_nA$ and $P_mA$ are CTAs.

This invention provides a free radical polymerization process with living characteristics which process comprises polymerizing one or more free radically polymerizable monomers in the presence of a source of initiating free radicals and a chain transfer agent (CTA) of Formula C or D which CTA during the polymerization reacts with the initiating or propagating radicals to give both a new radical that initiates further polymerization and a polymeric CTA also of Formula C or D (where R is the former initiating or propagating radical) with similar characteristics to the original CTA, the reaction conditions being chosen so that the ratio of the total number of initiator-derived radicals to the number of CTA molecules is maintained at a minimum value consistent with achieving an acceptable rate of polymerization, preferably less than 0.1, and the chain transfer constants of the CTAs are greater than 0.1, preferably greater than 1, and more preferably, greater than 10.

Initiating radicals are free radicals that are derived from the initiator or other species which add monomer to produce propagating radicals. Propagating radicals are radical species that have added one or more monomer units and are capable of adding further monomer units.

All of the benefits which derive from the use of radical polymerization can now be realized in syntheses of low polydispersity homo- and copolymers. The ability to synthesize block, graft, star, gradient and end-functional polymers further extends the value of the process as does compatibility with protic monomers and solvents.

The source of initiating radicals can be any suitable method of generating free radicals such as the thermally induced homolytic scission of a suitable compound(s) (thermal initiators such as peroxides, peroxyesters, or azo compounds), the spontaneous generation from monomer (e.g., styrene), redox initiating systems, photochemical initiating systems or high energy radiation such as electron beam, X- or gamma-radiation. The initiating system is chosen such that under the reaction conditions there is no substantial adverse interaction of the initiator or the initiating radicals with the transfer agent under the conditions of the experiment. The initiator should also have the requisite solubility in the reaction medium or monomer mixture.

Thermal initiators are chosen to have an appropriate half life at the temperature of polymerization. These initiators can include one or more of the following compounds: 2,2'-azobis(isobutyronitrile), 2,2'-azobis(2-cyano-2-butane), dimethyl 2,2'-azobisdimethylisobutyrate 4,4'-azobis(4-cyanopentanoic acid), 1,1'-azobis(cyclohexanecarbonitrile), 2-(t-butylazo)-2-cyanopropane, 2,2'-azobis[2-methyl-N-(1,1)-bis(hydroxymethyl)-2-hydroxyethyl] propionamide, 2,2'-azobis[2-methyl-N-hydroxyethyl)]-propionamide, 2,2'-azobis(N,N'-dimethyleneisobutyramidine)dihydrochloride, 2,2'-azobis (2-amidinopropane)dihydrochloride, 2,2'-azobis(N,N'-dimethyleneisobutyramine), 2,2'-azobis(2-methyl-N-[1,1-bis(hydroxymethyl)-2-hydroxyethyl]propionamide), 2,2'-azobis(2-methyl-N-[1,1-bis(hydroxymethyl)ethyl] propionamide), 2,2'-azobis[2-methyl-N-(2-hydroxyethyl) propionamide], 2,2'-azobis(isobutyramide)dihydrate, 2,2'-azobis(2,2,4-trimethylpentane), 2,2'-azobis(2-methylpropane), t-butyl peroxyacetate, t-butyl peroxybenzoate, t-butyl peroxyoctoate, t-butyl peroxyneodecanoate, t-butylperoxy isobutyrate, t-amyl peroxypivalate, t-butyl peroxypivalate, di-isopropyl peroxydicarbonate, dicyclohexyl peroxydicarbonate, dicumyl peroxide, dibenzoyl peroxide, dilauroyl peroxide, potassium peroxydisulfate, ammonium peroxydisulfate, di-t-butyl hyponitrite, dicumyl hyponitrite.

Photochemical initiator systems are chosen to have the requisite solubility in the reaction medium or monomer mixture and have an appropriate quantum yield for radical production under the conditions of the polymerization. Examples include benzoin derivatives, benzophenone, acyl phosphine oxides, and photo-redox systems.

Redox initiator systems are chosen to have the requisite solubility in the reaction medium or monomer mixture and have an appropriate rate of radical production under the conditions of the polymerization; these initiating systems can include combinations of the following oxidants and reductants:

oxidants: potassium peroxydisulfate, hydrogen peroxide, t-butyl hydroperoxide.

reductants: iron (II), titanium (III), potassium thiosulfite, potassium bisulfite.

Other suitable initiating systems are described in recent texts. See, for example, Moad and Solomon "The Chemistry of Free Radical Polymerization", Pergamon, London, 1995, pp 53-95.

The process of the invention can be applied to any monomers or monomer combinations which are susceptible to free-radical polymerization. Such monomers include those with the general structure:

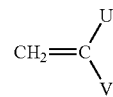

where U and V are as defined above. Optionally, the monomers are selected from the group that consists of maleic anhydride, N-alkylmaleimide, N-arylmaleimide, dialkyl fumarate and cyclopolymerizable monomers. Monomers $CH_2$=CUV as used herein include acrylate and methacrylate esters, acrylic and methacrylic acid, styrene, acrylamide, methacrylamide, and methacrylonitrile, mixtures of these monomers, and mixtures of these monomers with other monomers. As one skilled in the art would recognize, the choice of comonomers is determined by their steric and electronic properties. The factors which determine copolymerizability of various monomers are well documented in the art. For example, see: Greenley, R. Z., in Polymer Handbook 3rd Edition (Brandup, J., and Immergut, E. H. Eds.) Wiley: New York, 1989 p II/53.

Specific monomers or comonomers include the following: methyl methacrylate, ethyl methacrylate, propyl methacrylate (all isomers), butyl methacrylate (all isomers), 2-ethylhexyl methacrylate, isobornyl methacrylate, methacrylic acid, benzyl methacrylate, phenyl methacrylate, methacrylonitrile. alpha-methylstyrene, methyl acrylate, ethyl acrylate, propyl acrylate (all isomers), butyl acrylate (all isomers), 2-ethylhexyl acrylate, isobornyl acrylate, acrylic acid; benzyl acrylate, phenyl acrylate, acrylonitrile, styrene, functional methacrylates, acrylates and styrenes selected from glycidyl methacrylate, 2-hydroxyethyl methacrylate, hydroxypropyl methacrylate (all isomers), hydroxybutyl methacrylate (all isomers), N,N-dimethylaminoethyl methacrylate, N,N-diethylaminoethyl methacrylate, triethyleneglycol methacrylate, itaconic anhydride, itaconic acid, glycidyl acrylate, 2-hydroxyethyl acrylate, hydroxypropyl acrylate (all isomers), hydroxybutyl acrylate (all isomers), N,N-dimethylaminoethyl acrylate, N,N-diethylaminoethyl acrylate, triethyleneglycol acrylate, methacrylamide, N-methylacrylamide, N,N-dimethylacrylamide, N-tert-butylmethacrylamide, N-n-butylmethacrylamide, N-methylolmethacrylamide, N-ethylolmethacrylamide, N-tert-butylacrylamide, N-n-butylacrylamide, N-methylolacrylamide, N-ethylolacrylamide, vinyl benzoic acid (all isomers), diethylaminostyrene (all isomers), alpha-methylvinyl benzoic acid (all isomers), diethylamino alpha-methylstyrene (all isomers), p-vinylbenzene sulfonic acid, p-vinylbenzene sulfonic sodium salt, trimethoxysilylpropyl methacrylate, triethoxysilylpropyl methacrylate, tributoxysilylpropyl methacrylate, dimethoxymethylsilylpropyl methacrylate, diethoxymethylsilylpropyl methacrylate, dibutoxymethylsilylpropyl methacrylate, diisopropoxymethylsilylpropyl methacrylate, dimethoxysilylpropyl methacrylate, diethoxysilylpropyl methacrylate, dibutoxysilylpropyl methacrylate, diisopropoxysilylpropyl methacrylate, trimethoxysilylpropyl acrylate, triethoxysilylpropyl acrylate, tributoxysilylpropyl acrylate, dimethoxymethylsilylpropyl acrylate, diethoxymethylsilylpropyl acrylate, dibutoxymethylsilylpropyl acrylate, diisopropoxymethylsilylpropyl acrylate, dimethoxysilylpropyl acrylate, diethoxysilylpropyl acrylate, dibutoxysilylpropyl acrylate, diisopropoxysilylpropyl acrylate, vinyl acetate, vinyl butyrate, vinyl benzoate, vinyl chloride, vinyl fluoride, vinyl bromide, maleic anhydride, N-phenylmaleimide, N-butylmaleimide, N-vinylpyrrolidone, N-vinylcarbazole, butadiene, isoprene, chloroprene, ethylene, propylene.

EXAMPLES OF MULTIFUNCTIONAL (p≧2) STRUCTURES REPRESENTED BY FORMULA C

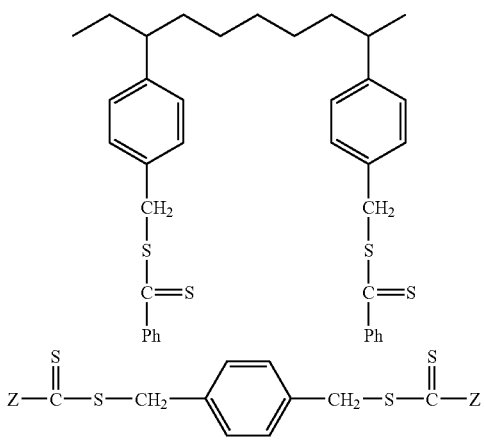

EXAMPLES OF MULTIFUNCTIONAL (m≧2) STRUCTURES REPRESENTED BY FORMULA D

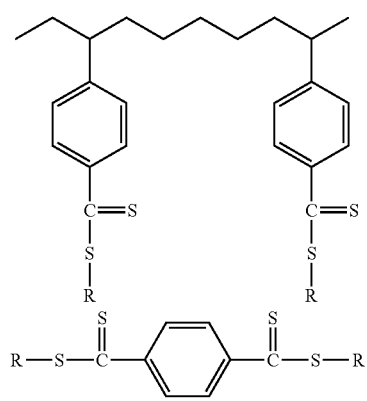

Many such structures are possible of which the following compounds are illustrative. Additional structures are found in the Examples section. In the compounds of Formulae C and D substituted rings can have reactive substituent groups directly or indirectly attached to the ring by means of a methylene group or other side chain.

The substituents on groups referred to above for R, R', R", Z, Z' in Formulae A-D and U, V, R" in the monomer do not take part in the polymerization reactions but form part of the terminal groups of the polymer chains and may be capable of subsequent chemical reaction. The low polydispersity polymer containing any such reactive group is thereby able to undergo further chemical transformation, such as being joined with another polymer chain. Suitable reactive substituents include: epoxy, hydroxy, alkoxy, acyl, acyloxy, carboxy (and salts), sulfonic acid (and salts), alkylcarbonyloxy, isocyanato, cyano, silyl, halo, and dialkylamino. Alternatively, the substituents may be non-reactive such as alkoxy, alkyl or aryl. Reactive groups should be chosen such that there is no adverse reaction with the CTA under the conditions of the experiment. For example, groups such as primary or secondary amino —$NH_2$, —NHalkyl) under some conditions may react with dithioesters to give thioamides thus destroying the CTA.

Unless specified otherwise alkyl groups referred to in this specification may be branched or unbranched and contain from 1 to 18 carbon atoms. Alkenyl groups may be branched or unbranched and contain from 2 to 18 carbon atoms. Saturated, unsaturated, or aromatic carbocyclic or heterocyclic rings may contain from 3 to 14 atoms.

"Heterocyclic" or "heterocyclyl" means a ring structure containing 3 to 10 atoms at least one of which is selected from O, N and S, which may or may not be aromatic. Examples of aromatic "heterocyclyl" moieties are pyridyl, furanyl, thienyl, piperidinyl, pyrrolidinyl, pyrazoyl, benzthiazolyl, indolyl, benzofuranyl, benzothiophenyl, pyrazinyl, quinolyl, and the like, optionally substituted with one or more alkyl, haloalkyl, halo, nitro, or cyano groups. "Ph" means phenyl.

An example of the preferred class of CTAs are the dithioesters (Formula C, p=1) such as are depicted in Scheme 2 which is illustrative of the reaction mechanism believed to be operative in the process of this invention. It should be understood, however, that the invention is not limited to the mechanism depicted and that other mechanisms may be involved.

Scheme 2:

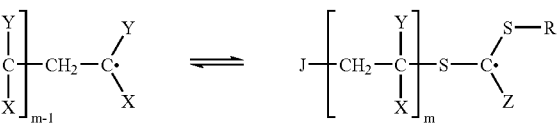

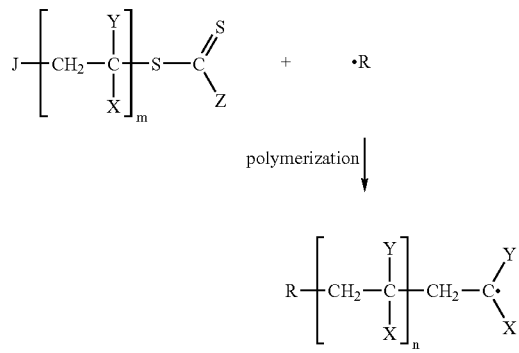

J is a fragment derived from an initiating or propagating radical.

A key feature of the invention, is the retention of the active thiocarbonylthio end group[—C(S)—S—] in the polymeric product. The invention thus also provides a route to block polymers as illustrated, for example, in Scheme 3.

J is a fragment derived from an initiating or a propagating radical.

Polymers with complex architectures including multi-block, branched, star and graft polymers are available through the use of reagents containing multiple thiocarbo- Scheme 3:

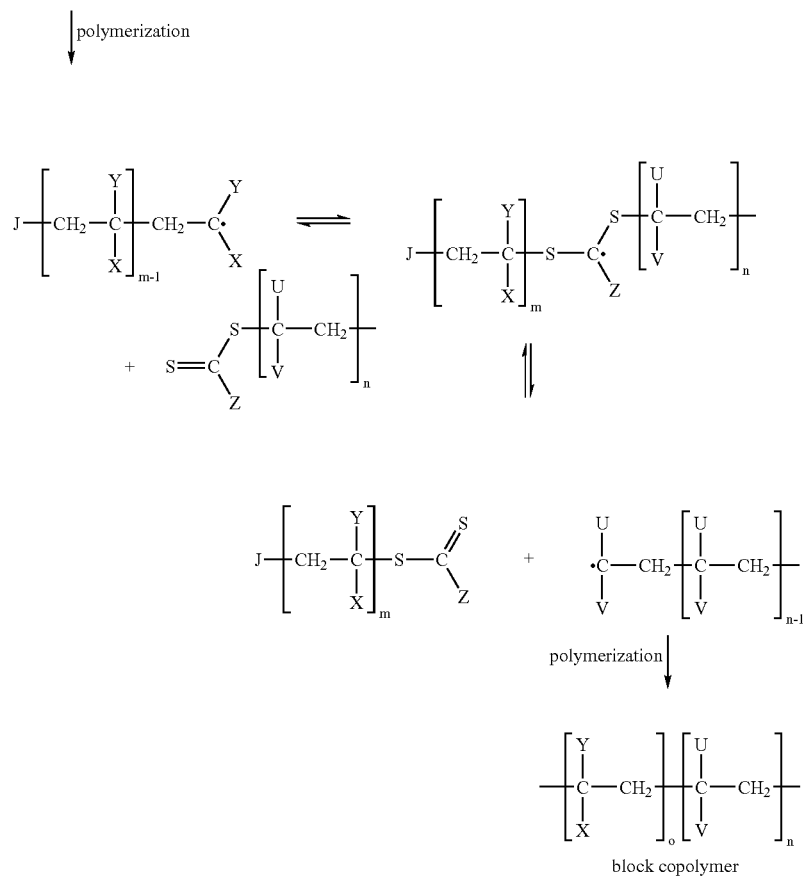

nylthio groups as indicated by formulae C (where $p \geq 2$) and D. The overall process is shown in Scheme 4.

Scheme 4:
Formation of linear polymer from CTA of formula C, p = 1

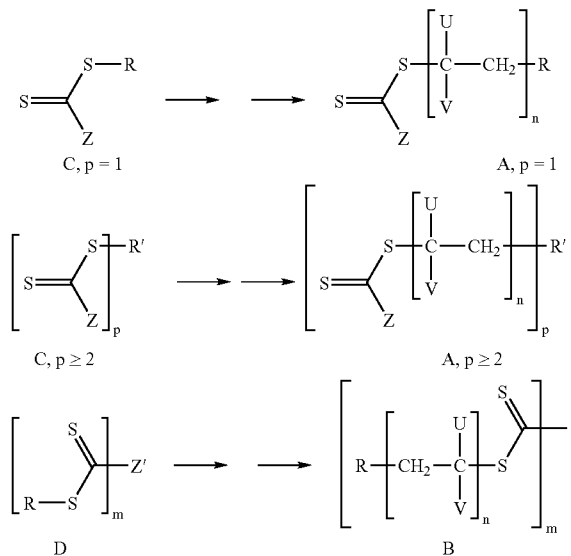

Block, star or graft polymers can be formed from polymers (prepared by any polymerization mechanism) that contain the thiocarbonylthio [—S—C(=S)—] linkage. Methods for forming dithoester and related groups are well-documented in the art. The following example (Scheme 5) of forming a block copolymer from poly(ethylene oxide) is illustrative of the process.

Scheme 5:

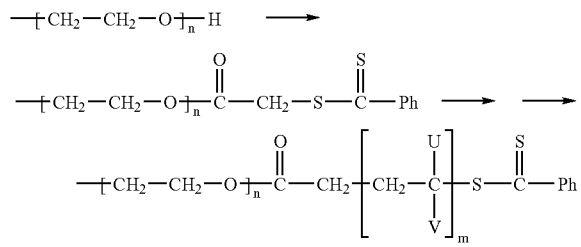

Benefits of the polymerization process described in this invention are:

a) Low polydispersity polymers can be synthesized.

In the context of the present invention, low polydispersity polymers are those with polydispersities that are significantly less than those produced by conventional free radical polymerization. In conventional free radical polymerization, polydispersities (the polydispersity is defined as the ratio of the weight average and number average molecular weights—$M_w/M_n$) of the polymers formed are typically in the range 1.6-2.0 for low conversions (<10%) and are substantially greater than this for higher conversions. Polydispersities obtained with the present invention are usually less than 1.5, often less than 1.3 and, with appropriate choice of the chain transfer agent and the reaction conditions, may be less than 1.1. The low polydispersity can be maintained at high conversions (see Examples).

Note that it is also possible to produce polymers with broad, yet controlled, polydispersity or multimodal molecular weight distribution by controlled addition of the CTA over the course of the polymerization process.

Müller et al. have derived relationships which enable polydispersities to be estimated for polymerizations which involve chain equilibration by reversible chain transfer (Müller, A. H. E.; Zhuang, R.; Yan, D.; Litvenko, G. *Macromolecules*, 1995, 28, 4326)

$$M_w/M_n = 1 + 1/C_{tr}.$$

This above relationship should apply to batch polymerizations carried to full conversion in the situation where the number of initiator-radical derived chains is small with respect to total chains and there are no side reactions.

This relationship suggests that the transfer constant should be >2 to obtain a polydispersity <1.5 in a batch polymerization. If the transfer constant is <2, low polydispersities (<1.5) may still be obtained in feed polymerization processes by choosing an appropriate monomer to transfer agent ratio and continuing the polymerization for a sufficient period to produce the desired molecular weight and polydispersity. In these circumstances, kinetic simulation can be used to aid in selecting reaction conditions.

In theory, it is possible to use reagents with very low transfer constants (<0.1). However, in this case it is likely that side reactions will complicate the polymerization process. In practice, polydispersities are likely to be higher than predicted by these relationships because of the limitations already mentioned. Nonetheless, these relationships serve as a useful guide in selecting reaction conditions.

b) Molecular weights increase in a predictable and linear manner with conversion (see Examples) which is controlled by the stoichiometry. In the case of monofunctional CTAs of Formulae C and D the molecular weight of the product can be calculated according to the relationship:

$$MW_{prod} = \frac{[\text{moles monomer consumed}]}{[\text{moles CTA}]} \times MW_{mon} + MW_{cta}$$

Where: $MW_{prod}$ is the number average molecular weight of the isolated polymer $MW_{mon}$ is the molecular weight of the monomer $MW_{cta}$ is the molecular weight of the CTA of formula C or D.

This expression applies under reaction conditions where the number of initiator-derived chains is small with respect to total chains. Note that this form of molecular weight control is very different to that seen in free radical polymerization in the presence of conventional transfer agents.

c) The process can be used to provide various low polydispersity polymers including:
End-functional polymers
Block and multiblock and gradient polymers
Star polymers
Graft or branched polymers.

d) The process of this invention is compatible with a wider range of monomers and reaction conditions than other processes for producing low polydispersity and reactive polymers. Specific advantages of the present process are:
i) The much higher transfer constant of compounds of Formula C or D (transfer constant can be >20) in comparison to macromonomers (transfer constant <2) means that it is not necessary to use starved-feed conditions to obtain low polydispersity polymers or block polymers. It is possible to use a batch polymerization process (see Examples).

ii) The compounds of Formula C or D do not undergo copolymerization with monomers. Therefore, low polydispersity polymers based on monosubstituted monomers (e.g., acrylic monomers, styrene) can be carried out under a wider range of reaction conditions.

The choice of the CTA compound is important in synthesis of low polydispersity polymers. The preferred dithioesters and related compounds give chain transfer with high chain transfer constants.

The transfer constant is defined as the ratio of the rate constant for chain transfer to the rate constant for propagation at zero conversion of monomer and CTA compound. If chain transfer occurs by addition-fragmentation, the rate constant for chain transfer ($k_{tr}$) is defined as follows:

$$k_{tr} = k_{add} \times \frac{k_\beta}{k_{-add} + k_\beta}$$

where $k_{add}$ is the rate constant for addition to the CTA and $k_{-add}$ and $k_b$ are the rate constants for fragmentation in the reverse and forward directions respectively. Based on the addition-fragmentation mechanism, four factors can be seen to influence the effectiveness of the CTA in the process of this invention:

a) The rate of reaction of the CTA (RA and $AP_n$ in Scheme 1).
b) The partitioning of the intermediate radicals ($P_nA.R$ and $P_nA.P_m$ in Scheme 1) between starting materials and products.
c) The rate of fragmentation of the intermediate radicals ($P_nA.R$ and $P_nA.P_m$ in Scheme 1).
d) The ability of the expelled radicals (R. and $P_n$. in Scheme 1) to reinitiate polymerization. Factors a) and b) determine thee magnitude of the transfer constant of the CTA compound.

Preferably, the transfer constant for the addition-fragmentation chain transfer process is >0.1. The polydispersity obtained under a given set of reaction conditions is sensitive to the value of the transfer constant. Lower polydispersities will result from the use of reagents with higher transfer constants. Benzyl dithiobenzoate derivatives have transfer constants which are estimated to be >20 in polymerization of styrene or acrylate esters. Higher transfer constants also allow greater flexibility in the choice of reaction conditions. For reagents with low chain transfer constants, the use of feed addition is advantageous to obtain low polydispersities.

The chain transfer activity of CTAs of Formula C or D is a function of the substituents R and Z and the particular propagating radical. R should be chosen so as to be a free radical leaving group under the polymerization conditions (and yet retain ability to reinitiate polymerization—see below). In styrene polymerization, dithiobenzoate CTAs (RA in Scheme 1) where A is $PhCS_2$— and R is —$C(Me)_2$Ph, —$C(Me)_2$CN, —$C(Me)_2CO_2$Alkyl, —$C(Me)_2CH_2C(Me)_3$, —$C(Me)_3$, —$C(Me)_3$, —$C(Me)HPh$, —$CH_2Ph$, —$CH_2CO_2H$ are all effective in giving narrowed polydispersity and molecular weight control under batch polymerization conditions (see Examples). On the other hand, in MMA polymerization, effectiveness decreases in the order where R is: —$C(Me)_2Ph^3$—$C(Me)_2CN$>—$C(Me)_2CO_2Alkyl$>—$C(Me)_2CH_2C(Me)_3$, —$C(Me)_3$>—$C(Me)HPh$>—$CH_2Ph$. Of these reagents, only those dithiobenzoates where R=—$C(Me)_2Ph$ or —$C(Me)_2CN$ are effective in giving both narrowed polydispersity and molecular weight control under batch polymerization conditions. The dithiobenzoate where R=—$C(Me)_2CO_2Et$ provides good molecular weight control but broader polydispersity. These results can be related to the magnitude of the transfer is constant for the CTA and to the free radical leaving group ability of the R substituent with respect to that of the propagating radical. For example, the dithiobenzoates with R=—$C(Me)HPh$ and —$CH_2Ph$, which are ineffective in providing living characteristics to the batch polymerization of MMA at 60° C., have transfer constants of 0.15 and 0.03 respectively. These R groups are poor free radical leaving groups with respect to the MMA propagating radical.

It is also important to bear these considerations in mind in block copolymer synthesis. For example, the polystyryl propagating species (—$P_n$=—[$CH_2$—$CHPh$]$_n$ in Scheme 1) is a poorer free radical leaving group than the poly(methyl methacrylate) propagating species (—$P_n$=—[$CH_2$—$C(Me)(CO_2Me)$]$_n$ in Scheme 1). Thus, for synthesis of poly(methyl methacrylate-block-styrene) under batch polymerization conditions the poly(methyl methacrylate) block is made first in order to make a narrow polydispersity block copolymer.

If the reaction is carried out under conditions whereby the monomer is fed to maintain a lower monomer to CTA ratio, reagents with lower transfer constants can be used successfully. Thus, a polystyrene polymeric CTA has been successfully converted to poly(methyl methacrylate-block-styrene) under feed polymerization conditions.

Z in formulae C and D should be chosen to give a high reactivity of the double bond towards addition (while not slowing the rate of fragmentation to the extent that there is an unacceptable retardation of polymerization—see below). For example, the transfer constant increases in the series where Z=—$NMe_2$<—OMe<—SMe<—Me<—Ph. The compound Z=$NEt_2$, R=$CH_2Ph$ has a very low transfer constant (<0.01) and is ineffective in polymerizations of styrene and methyl methacrylate and vinyl acetate. Xanthate esters (Z=—O-alkyl) also have low transfer constants in polymerizations of styrene and methyl methacrylate (0.1) and are not effective in imparting living characteristics to polymerizations of these monomers. These compounds are not part of the present invention.

On the other hand, dithiocompounds with Z=—S-alkyl, -alkyl or -aryl (and other substituents as defined herein) have high transfer constants (the compound Z=Ph, R=$CH_2Ph$ has a transfer constant of >20 in styrene polymerization at 60° C.) and are effective.

Factors c) and d), as set out above, determine whether or not there is retardation of polymerization and the extent of any retardation. If the overall rate of reinitiation is greater than or equal to the rate of propagation there will be no retardation. These factors will be influenced by the substituents R and Z in formulae C and D and the nature of the propagating radical.

We have also found that the relative rates of addition and of fragmentation can be estimated using molecular orbital calculations (For details of the method see Moad, G., Moad, C. L., Rizzardo, E., and Thang, S. H., *Macromolecules*, 1996, 29, 7717). This method and information on radical reactivities (see for example Moad and Solomon "The Chemistry of Free Radical Polymerization", Pergamon, London, 1995), when taken together with the information provided herein, will assist those skilled in the art in selecting transfer agents for particular polymerizations.

For heterogeneous polymerization, it is desirable to choose a CTA which has appropriate solubility parameters. For aqueous emulsion polymerization, the CTA should preferably partition in favour of the organic (monomer) phase and yet have sufficient aqueous solubility that it is able to distribute between the monomer droplet phase and the polymerization locus.

The choice of polymerization conditions is also important. The reaction temperature will influence the rate parameters discussed above. For example, higher reaction temperatures will typically increase the rate of fragmentation. Conditions should be chosen such that the number of chains formed from initiator-derived radicals is minimized to an extent consistent with obtaining an acceptable rate of polymerization. Termination of polymerization by radical-radical reaction will lead to chains which contain no active group and therefore cannot be reactivated. The rate of radical-radical termination is proportional to the square of the radical concentration. Furthermore, in the synthesis of block star or branched polymers, chains formed from initiator-derived radicals will constitute a linear homopolymer impurity in the final product. These reaction conditions therefore require careful choice of the initiator concentration and, where appropriate, the rate of the initiator feed.

It is also desirable to choose other components of the polymerization medium (for example, the solvents, surfactants, additives, and initiator) such that they have a low transfer constant towards the propagating radical. Chain transfer to these species will lead to the formation of chains which do not contain the active group.

As a general guide in choosing conditions for the synthesis of narrow polydispersity polymers, the concentration of initiator(s) and other reaction conditions (solvent(s) if any, reaction temperature, reaction pressure, surfactants if any, other additives) should be chosen such that the molecular weight of polymer formed in the absence of the CTA is at least twice that formed in its presence. In polymerizations where termination is solely by disproportionation, this equates to choosing an initiator concentration such that the total moles of initiating radicals formed during the polymerization is less than 0.5 times that of the total moles of CTA. More preferably, conditions should be chosen such that the molecular weight of polymer formed in the absence of the CTA is at least 5-fold that formed in its presence ([initiating radicals]/[CTA]<0.2).

Thus, the polydispersity can be controlled by varying the number of moles of CTA to the number of moles initiating radicals. Lower polydispersities are obtained by increasing this ratio; higher polydispersities are obtained by decreasing this ratio.

With these provisos, the polymerization process according to the present invention is performed under the conditions typical of conventional free-radical polymerization. Polymerization employing the above described CTAs is suitably carried out with temperatures during the reaction in the range −20 to 200° C., preferably in the range 40-160° C.

The process of this invention can be carried out in emulsion, solution or suspension in either a batch, semi-batch, continuous, or feed mode. Otherwise-conventional procedures can be used to produce narrow polydispersity polymers. For lowest polydispersity polymers, the CTA is added before polymerization is commenced. For example, when carried out in batch mode in solution, the reactor is typically charged with CTA and monomer or medium plus monomer. To the mixture is then added the desired amount of initiator and the mixture is heated for a time which is dictated by the desired conversion and molecular weight. Polymers with broad, yet controlled, polydispersity or with multimodal molecular weight distribution can be produced by controlled addition of the CTA over the course of the polymerization process.

In the case of emulsion or suspension polymerization the medium will often be predominantly water and the conventional stabilizers, dispersants and other additives can be present. For solution polymerization, the reaction medium can be chosen from a wide range of media to suit the monomer(s) being used.

As has already been stated, the use of feed polymerization conditions allows the use of CTAs with lower transfer constants and allows the synthesis of block polymers that are not readily achieved using batch polymerization processes. If the polymerization is carried out as a feed system the reaction can be carried out as follows. The reactor is charged with the chosen medium, the CTA and optionally a portion of the monomer(s). Into a separate vessel is placed the remaining monomer(s). Initiator is dissolved or suspended in reaction medium in another separate vessel. The medium in the reactor is heated and stirred while the monomer+medium and initiator+medium are introduced, for example by a syringe pump or other pumping device. The rate and duration of feed is determined largely by the quantity of solution, the desired monomer/CTA/initiator ratio and the rate of the polymerization. When the feed is complete, heating can be continued for an additional period.

Following completion of the polymerization, the polymer can be isolated by stripping off the medium and unreacted monomer(s) or by precipitation with a non-solvent. Alternatively, the polymer solution/emulsion can be used as such, if appropriate to its application.

The invention has wide applicability in the field of free radical polymerization and can be used to produce polymers and compositions for coatings, including clear coats and base coat finishes or paints for automobiles and other vehicles or maintenance finishes for a wide variety of substrates. Such coatings can further include pigments, durability agents, corrosion and oxidation inhibitors, rheology control agents, metallic flakes and other additives. Block and star, and branched polymers can be used as compatibilisers, thermoplastic elastomers, dispersing agents or rheology control agents. Additional applications for polymers of the invention are in the fields of imaging, electronics (e.g., photoresists), engineering plastics, adhesives, sealants, and polymers in general.

Preferred chain transfer agents applicable in the process of this invention are as follows:

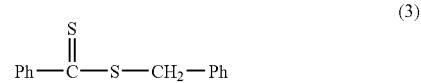

(3)

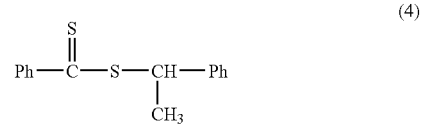

(4)

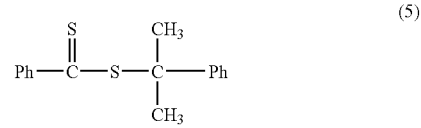

(5)

-continued (6) Ph−C(=S)−S−CH(CH₃)−OAc (7) 1,2,3,4,5,6-hexakis(CH₂SC(S)Z)benzene (8) Z−CS₂−CH₂−C₆H₄−CH₂−SC(S)−Z (para)

(9) 1,2,4,5-tetrakis(CH₂SC(S)Z)benzene

(10) Z−CS₂−C(CH₃)₂−C₆H₄−C(CH₃)₂−SC(S)−Z

(11) Ph−C(=S)−S−CH(CH₃)−C₆H₄−OCH₃

(12) CH₃−C(=S)−S−CH₂Ph

(13) CH₃−C(=S)−S−CH₂−COOEt

(14) Ph−C(=S)−S−C(CH₃)₂−COOEt

(15) Ph−C(=S)−S−C(CH₃)₂−CN

(16) Ph−C(=S)−S−C(CH₃)₂−CH₃

(17) Ph−C(=S)−S−C(CH₃)₂−CH₂−C(CH₃)₂−CH₃

(18) Ph−C(=S)−S−C(CH₃)₂−C₆H₄−Cl

(19) Ph−C(=S)−S−CH₂−C₆H₄−CH=CH₂

(20) (C₂H₅O)₂P(=O)−C(=S)−S−CH₂−Ph

(21) Ph−C(=S)−S−S−C(CH₃)₃

(22) Cl−C₆H₄−C(=S)−S−C(CH₃)₂−Ph

(23) (1-naphthyl)−C(=S)−S−C(CH₃)₂−Ph

(24) Ph−C(=S)−S−C(CH₃)(CN)−CH₂CH₂COOH

(25) PhCH₂−S−C(=S)−C₆H₄−C(=S)−S−CH₂Ph

(26) PhCH₂−S−C(=S)−S−CH₂Ph

(27) Ph−C(=S)−S−CH₂−COOH

(28) Ph−C(=S)−S−CH₂−CO₂−(CH₂−CH₂−O)ₙ−CH₃  and

(29) Ph−C(=S)−S−C(CH₃)(CN)−CH₂CH₂CO₂−(CH₂−CH₂−O)ₙ−CH₃ wherein Z is phenyl.

EXAMPLES 1 TO 18

Preparation of Thiocarbonylthio Compounds

The processes for making compounds (3) to (29) are as follows: Procedures 1-11 describe the preparation of known CTA compounds. Examples 1-18 describe the synthesis of novel CTA compounds.

Procedure 1

Preparation of Dithiobenzoic acid and 4-chlorodithiobenzoic acid

Dithiobenzoic acid and 4-chlorodithiobenzoic acid were prepared according to known procedures. For instance, see the method described in German Patent 1,274,121 (1968); (CA70: 3573v).

Procedure 2

Preparation of benzyl dithiobenzoate (3) (C, p=1, R=CH$_2$Ph, Z=Ph)

This title compound was prepared by a modification of the one-pot procedure described in *Recueil*, 92, 601 (1973). Phenyl magnesium bromide was prepared from bromobenzene (62.8 g) and magnesium turnings (10 g) in dry tetrahydrofuran (300 mL). The solution was warmed to 40° C. and carbon disulfide (30.44 g) was added over 15 minutes whilst maintaining the reaction temperature at 40° C. To the resultant dark brown mixture was added benzyl bromide (76.95 g) over 15 minutes. The reaction temperature was raised to 50° C. and maintained at that temperature for a further 45 minutes. Ice water (1.5 L) was added and the organic products extracted with diethyl ether (total 2 L). The ethereal phase was washed with water (1 L), brine (500 mL) and dried over anhydrous magnesium sulfate. After removal of solvent and vacuum distillation of the residue, benzyl dithiobenzoate (3) was obtained as a red oil (60.2 g, 61.7% yield), b.p. 152° C. (0.02 mmHg) [lit (Beilstein, EIII 9, 1998): b.p. 179-180° C. at 3 mmHg]. $^1$H-nmr (CDCl$_3$) d (ppm): 4.60 (s, 2H); 7.30-7.60 (m, 8H) and 8.02 (m, 2H).

Procedure 3

Preparation of 1-phenylethyl dithiobenzoate (4) (C, p=1, R=CH(CH$_3$)Ph, Z=Ph)

Dithiobenzoic acid (9.9 g), styrene (10 mL) and carbon tetrachloride (30 mL) were combined and the mixture heated at 70° C. for 4 hours. The resultant mixture was reduced to a crude oil. The yield of 1-phenylethyl dithiobenzoate (4) was 43.4% after purification by column chromatography (aluminium oxide (activity III), petroleum spirit 40-60° C. eluent). $^1$H-nmr (CDCl$_3$) d (ppm): 1.92 (d, 3H); 5.39 (q, 1H); 7.34-7.62 (m, 8H) and 8.08 (m, 2H).

Example 1

Preparation of 2-phenylprop-2-yl dithiobenzoate (5) (C, p=1, R=C(CH$_3$)$_2$Ph, Z=Ph)

A mixture of dithiobenzoic acid (10.59 g), a-methylstyrene (10 g) and carbon tetrachloride (40 mL) was heated at 70° C. for 4 hours. The resultant mixture was reduced to a crude oil which was purified by column chromatography (aluminium oxide (activity III), n-hexane eluent) to give 2-phenylprop-2-yl dithiobenzoate (5) (6.1 g, 32.6% yield) as a dark purple oil. $^1$H-nmr (CDCl$_3$) d(ppm): 2.03 (s, 6H); 7.20-7.60 (m, 8H) and 7.86 (m, 2H).

Example 2

Preparation of 1-acetoxyethyl dithiobenzoate (6) (C, p=1, R=CH(CH$_3$)OAc; Z=Ph)

A mixture of dithiobenzoic acid (4 g), vinyl acetate (10 mL) and carbon tetrachloride (15 mL) was heated at 70° C. for 16 hours. The resultant mixture was reduced and the residue purified by column chromatography (aluminium oxide column (activity III), n-hexane eluent) to give 1-acetoxyethyl dithiobenzoate (6) (3.21 g, 51.5% yield) as a dark red oil. $^1$H-nmr (CDCl$_3$) d (ppm): 1.80 (d, 3H); 2.09 (s, 3H); 6.75 (q, 1H); 7.34-7.60 (m, 3H) and 7.97 (m, 2H).

Example 3

Preparation of hexakis(thiobenzoylthiomethyl)benzene (9, Z=Ph) (C, p=6, R=C$_6$(CH$_2$)$_6$, Z=Ph)

Hexakis(thiobenzoylthiomethyl)benzene was prepared from hexakis(bromomethyl)benzene according to the method described for the preparation of benzyl dithiobenzoate (3) with the modification that the reaction mixture was heated at 50° C. for 3 hours. After the usual work-up, recrystallization from 1:4 chloroform/ethanol gave the title compound as a red solid (77% yield), m.p. 222-224° C. (dec). $^1$H-nmr (CDCl$_3$) d (ppm): 4.66 (s, 12H); 7.30-7.60 (m, 18H) and 7.94 (m, 12H).

Example 4

Preparation of 1,4-bis(thiobenzoylthiomethyl)benzene (8, Z=Ph) (C, p=2, R=C$_6$H$_4$(CH$_2$)$_2$, Z=Ph)

1,4-Bis(thiobenzoylthiomethyl)benzene was prepared from a,a'-dibromo-p-xylene according to the method described for the preparation of benzyl dithiobenzoate (3) with the modification that the reaction mixture was heated at 40° C. for 1.5 hours. After the usual work-up, recrystallization from ethanol gave the title compound as a red solid (66.7% yield), m.p. 95-97° C. $^1$H-nmr (CDCl$_3$) d (ppm); 4.60 (s, 4H); 7.34-7.60 (m, 6H) and 8.00 (m, 4H).

Example 5

Preparation of 1,2,4,5-tetrakis(thiobenzoylthiomethyl)benzene (9) (C, p=4, R=C$_6$H$_2$(CH$_2$)$_4$, Z=Ph)

1,2,4,5-Tetrakis(thiobenzoylthiomethyl)benzene was prepared from 1,2,4,5-tetrakis-(bromomethyl)benzene according to the method described for the preparation of benzyl dithiobenzoate (3) with the modification that the reaction mixture was heated at 40° C. for 1 hour. The usual work-up gave a red solid which was recrystallized from 1:4 benzene/ethanol to give 1,2,4,5-tetrakis(thiobenzoylthiomethyl)benzene (47% yield), m.p. 142-143.5° C. (dec). $^1$H-nmr (CDCl$_3$) d (ppm): 4.65 (s, 8H); 7.30-7.58 (m, 14H) and 7.97 (m, 8H).

Example 6

Preparation of 1,4-bis-(2-(thiobenzoylthio)prop-2-yl)benzene (10) (C, p=2, R=1,4-C$_6$H$_4$(C(CH$_3$)$_2$)$_2$, Z=Ph)

1,4-diisopropenylbenzene (3.96 g) was added to a solution of dithiobenzoic acid (8 g) in carbon tetrachloride (50 mL) and the mixture heated at 70° C. for 16 hours. Removal of the solvent, followed by trituration with 1:2 diethyl ether/n-hexane allowed isolation of the title compound as a purple solid (2.87 g, 24.6% yield), m.p. 143-145° C. (dec.). $^1$H-nmr (CDCl$_3$) d (ppm): 2.00 (s, 12H); 7.33 (m, 4H); 7.49 (m, 2H); 7.50 (s, 4H) and 7.86 (m, 4H).

Example 7

Preparation of 1-(4-methoxyphenyl)ethyl dithiobenzoate (11) (C, p=1, R=4—CH$_3$OC$_6$H$_4$(CH$_3$)CH; Z=Ph)

A mixture of dithiobenzoic acid (3.6 g), 4-vinylanisole (2.9 g) and carbon tetrachloride (20 mL) were heated at 70° C. overnight. The solvent was evaporated and the residue subjected to column chromatography (aluminium oxide (activity III) column, 2% diethyl ether in n-hexane eluent) which gave the title compound (53% yield). $^1$H-nmr (CDCl$_3$) d (ppm): 1.80 (d, 3H, SCHCH$_3$); 3.80 (s, 3H, OCH$_3$); 5.22 (q, 1H, SCHCH$_3$) and 6.88-7.97 (m, 9H, ArH).

Procedure 4

Preparation of benzyl dithioacetate (12) (C, p=1, R=CH$_2$Ph; Z=CH$_3$)

Methyl magnesium chloride (10 mL, 3M solution in THF) was diluted with THF (10 mL) and the resulting solution warmed to 40° C. Carbon disulfide (2.28 g, 0.03 mol) was added over 10 minutes while maintaining the reaction temperature at 40° C. The reaction was cooled to room temperature before adding benzyl bromide (5.1 g, 0.03 mol) over 15 minutes. The reaction temperature was increased to 50° C. and maintained for a further 45 minutes. Water (100 mL) was added and the organic products extracted with n-hexane (3×60 mL). The combined organic extracts were washed with water, brine and dried over anhydrous magnesium sulfate. After removal of solvent and column chromatography (Kieselgel-60, 70-230 mesh, 5% diethyl ether in n-hexane eluent), pure benzyl dithioacetate was obtained as a golden oil (3 g, 55% yield). $^1$H-nmr (CDCl$_3$) d(ppm): 2.90 (s, 3H); 4.46 (s, 2H) and 7.31 (m, 5H).

Procedure 5

Preparation of ethoxycarbonylmethyl dithioacetate (13) (C, p=1, R=CH$_2$COOEt; Z=CH$_3$)

Methyl magnesium chloride (10 mL, 3M solution in THF) was diluted with THF (10 mL) and the resulting solution warmed to 40° C. Carbon disulfide (2.28 g, 0.03 mol) was added over 10 minutes while maintaining the reaction temperature at 40° C. The reaction was cooled to room temperature before adding ethyl bromoacetate (5.01 g, 0.03 mol) over 15 minutes. The reaction temperature was increased to 50° C. and maintained for a further 4 hours. Water (100 mL) was added and the organic products were extracted with ethyl acetate (3×60 mL). The combined organic extracts were washed with water, brine and dried over anhydrous magnesium sulfate. After removal of solvent and column chromatography (Kieselgel-60, 70-230 mesh, 10% diethyl ether in n-hexane eluent), pure ethoxycarbonylmethyl dithioacetate was obtained as a golden oil (1.3 g, 24.3% yield). $^1$H-nmr (CDCl$_3$) d(ppm): 1.25 (t, 3H); 2.90 (s, 3H); 4.07 (s, 2H) and 4.20 (q, 2H).

Example 8

Preparation of 2-(ethoxycarbonyl)prop-2-yl dithiobenzoate (14) (C, p=1, R=C(CH$_3$)$_2$COOEt; Z=Ph)

Phenyl magnesium bromide was prepared from bromobenzene (6.28 g, 0.04 mol) and magnesium turnings (1 g) in dry THF (30 mL). The solution was warmed to 40° C. and carbon disulfide (3.05 g, 0.04 mol) was added over 15 minutes while maintaining the reactions temperature at 40° C. To the resultant dark brown solution Was added ethyl a-bromoisobutyrate (7 g, 0.036 mol). The reaction temperature was raised to 80° C. and maintained for 60 hours. Ice water (50 mL) was added and the organic products were extracted with diethyl ether (3×50 mL). The combined organic extracts were washed with water, brine and dried over anhydrous magnesium sulfate. After removal of solvent and purification by column chromatography (Kieselgel-60, 70-230 mesh, n-hexane/diethyl ether (9:1) eluent), 2-(ethoxycarbonyl)prop-2-yl dithiobenzoate was obtained as a red oil (4.52 g, 42.2% yield). $^1$H-nmr (CDCl$_3$) d (ppm): 1.25 (t, 3H, CH$_2$CH$_3$), 1.77 (s, 6H, 2×CH$_3$), 4.17 (q, 2H, OCH$_2$CH$_3$), 7.35 (dd, 2H, meta-ArH), 7.52 (dd, 1H, para-ArH) and 7.95 (d, 2H, ortho-ArH).

Example 9

Preparation of 2-cyanoprop-2-yl dithiobenzoate (15) (C, p=1, R=C(CH$_3$)$_2$CN; Z=Ph)

2-Bromo-2-cyanopropane was prepared by the procedure of Chrzaszczewska and Popiel (*Roczniki Chem.*, 7, 74-8 (1927); *Chem. Abstr.* (1928) 22:1343$^6$). 2-Cyanoprop-2-yl dithiobenzoate (15) was prepared from 2-bromo-2-cyanopropane by a method similar to that used to prepare compound (14) with the modification that the reaction Was maintained at 50° C. for 24 hours. After work-up and purification (column chromatography on Kieselgel-60, 70-230 mesh, n-hexane/diethyl ether 9:1 eluent), 2-cyanoprop-2-yl dithiobenzoate (15) was obtained as a dark red oil (1.9 g, 43% yield). $^1$H-nmr (CDCl$_3$) d (ppm): 1.95 (s, 6H, 2×CH$_3$), 7.38 (dd, 2H, meta-ArH), 7.57 (dd, 1H para-ArH) and 7.92 (d, 2H, ortho-ArH). $^{13}$C-nmr (CDCl$_3$) d (ppm): 26.5, 41.7, 120.0 (CN), 126.6, 128.5, 132.9, 144.5 and 227.

Procedure 6

Preparation of Tert-butyl dithiobenzoate (16) (C, p=1, R=C(CH$_3$)$_3$; Z=Ph)

The synthesis of t-butyl dithiobenzoate (16) was carried out in two steps.

i) S-t-butyl Thiobenzoate t-Butyl Mercaptan (6.15 g, 0.068 mol) was added dropwise to a solution of benzoyl chloride (10.5 g, 0.075 mol) in pyridine (6 g). The resulting mixture was allowed to stir for two hours at room temperature then poured onto ice-water and the mixture extracted with diethyl ether. The organic extract was washed with dilute HCl, water and brine and finally dried over anhydrous sodium sulfate. After removal of solvent and vacuum distillation, S-t-butyl thiobenzoate was obtained (6.64 g, 50.1% yield), b.p. 86° C. (0.8 mmHg). $^1$H-nmr (CDCl$_3$) d (ppm): 1.60 (s, 9H, 3×CH$_3$), 7.41 (m, 2H, ArH), 7.54 (m, 1H, ArH) and 7.94 (d, 2H, ArH). $^{13}$C-nmr (CDCl$_3$) d (ppm): 29.8, 48.0, 126.8, 128.3, 132.7, 138.6 and 192.9.

ii) t-Butyl Dithiobenzoate

A mixture of S-t-butyl thiobenzoate (1.94 g, 0.01 mol) and Lawesson's reagent (2.43 g, 0.006 mol) in anhydrous toluene (10 mL) was refluxed for 25 hours. After cooling to room temperature, the reaction mixture was concentrated and the residue subjected to column chromatography (Kieselgel-60, 70-230 mesh, petroleum spirit/diethyl ether 19:1) The title compound was obtained as an oil, 1.37 g (65.5%). $^1$H-nmr (CDCl$_3$) d (ppm): 1.69 (s, 9H, 3×CH$_3$), 7.36 (m, 2H, meta-ArH), 7.50 (m, 1H, para-ArH) and 7.88 (d, 2H, ortho-ArH). $^{13}$C-nmr (CDCl$_3$) d (ppm): 28.2, 52.2, 126.6, 128.1, 131.7 and 147.0. The signal due to C=S (d>220.0 ppm) was beyond the frequency range of the spectrum.

Example 10

Preparation of 2,4,4-trimethylpent-2-yl dithiobenzoate (17) (C, p=1, R=C(CH$_3$)$_2$CH$_2$C(CH$_3$)$_3$; Z=Ph)

A mixture of dithiobenzoic acid (5 g), 2,4,4-trimethylpentene (7.3 g) and carbon tetrachloride (25 mL) was heated at 70° C. for two days. The resultant mixture was reduced to a crude oil. Purification of the residue, by column chromatography (Kieselgel-60, 70-230 mesh, petroleum spirit 40-60° C. eluent) gave 2,4,4-trimethylpent-2-yl dithiobenzoate (17) (2.74 g, 31.7% yield) as a dark red oil. $^1$H-nmr (CDCl$_3$) d (ppm): 1.08 (s, 9H, 3×CH$_3$), 1.77 (s, 6H, 2×CH$_3$), 2.26 (s, 2H, CH$_2$), 7.35 (dd, 2H, meta-ArH), 7.49 (dd, 1H, para-ArH) and 7.85 (d, 2H, ortho-ArH). $^{13}$C-nmr (CDCl$_3$) d (ppm): 28.3, 31.5, 32.8, 50.5, 57.7, 126.6, 128.1, 131.5 and 147.9. The signal due to C=S (d>220.0 ppm) was beyond the frequency range of the spectrum.

Example 11

Preparation of 2-(4-chlorophenyl)prop-2-yl dithiobenzoate (18) (C, p=1, R=4—ClC$_6$H$_4$(CH$_3$)$_2$C; Z=Ph)

Dithiobenzoic acid (6.3 g) and 4-chloro-a-methylstyrene (6 g) were combined and the mixture heated at 70° C. overnight. The residue was subjected to column chromatography (Kieselgel-60, 70-230 mesh, n-hexane as eluent) which gave the title compound as a purple solid (34.2% yield) m.p. 77-78° C. $^1$H-nmr (CDCl$_3$) d (ppm): 1.97 (s, 6H, 2×CH$_3$), 7.20-7.52 (m, 7H, ArH) and 7.86 (d, 2H, ArH). $^{13}$C-nmr (CDCl$_3$) d (ppm): 28.4, 55.7, 126.5, 128.1, 131.9, 132.4, 142.8, 146.0. The signal due to C=S (d>220.0 ppm) was beyond the frequency range of the spectrum.

Example 12

Preparation of 3- & 4-vinylbenzyl dithiobenzoates (19) (C, p=1, R=CH$_2$CHC$_6$H$_4$CH$_2$; Z=Ph)

A mixture of 3- & 4-vinylbenzyl dithiobenzoate (19) was synthesized from a mixture of 3- & 4-(chloromethyl)styrene by a procedure similar to that used for compound (14). The reaction was maintained at 50° C. for 24 hours. After work-up and column chromatography (aluminium oxide (activity II-III), n-hexane/diethyl ether 49:1 eluent) the mixture of 3- & 4-vinylbenzyl dithiobenzoate (19) was obtained in 42% yield as a red oil. $^1$H-nmr (CDCl$_3$) d (ppm): 4.60 (s, 2H, CH$_2$), 5.28 (d, 1H, CH$_2$=CH), 5.77 (d, 1H, CH$_2$=CH), 6.72 (dd, 1H, CH$_2$=CH), 7.20-7.60 (m, 7H, ArH) and 8.00 (d, 2H, ArH).

Procedure 7

Preparation of S-benzyl diethoxyphosphinyldithioformate (20) (C, p=1, R=CH$_2$Ph; Z=(EtO)$_2$P(O))

The title compound (20) was prepared by adapting the procedure described by Grisley, *J. Org. Chem.*, 26, 2544 (1961).

To a stirred slur of sodium hydride (60% dispersion in mineral oil) (8 g, 0.2 mol) in tetrahydrofuran (200 mL) was added diethyl phosphate. (27.5 g, 0.2 mol) dropwise under nitrogen. The mixture was stirred until hydrogen evolution ceased (about 15 minutes). The mixture was allowed to cool in an ice-water bath and carbon disulfide (76 g, 1 mol) was added over 15 minutes followed by benzyl chloride (25.2 g, 0.2 mol) in THF (100 mL) over 20 minutes. The resultant mixture was stirred at room temperature for 24 hours. Diethyl ether (200 mL) was added and the mixture washed with water (3×200 mL). The organic layer was dried (MgSO$_4$) filtered and evaporated in vacuo. After column chromatography (Kieselgel-60, 70-230 mesh, 1:4 ethyl acetate/n-hexane eluent), S-benzyl diethoxyphosphinyldithioformate (20) was obtained (11 g, 18% yield) as a red oil. $^1$H-nmr (CDCl$_3$) d (ppm) 1.43 (t, 6H); 4.38 (s, 2H), 4.65 (q, 4H) and 7.30-7.45 (m, 5H).

Procedure 8

Preparation of tert-butyl trithioperbenzoate (21) (C, p=1; R=(CH$_3$)$_3$CS; Z=Ph)

The title compound (21) was prepared according to the procedure described by Aycock and Jurch, *J. Org. Chem.*, 44, 569-572, (1979). The residue was subjected to column chromatography (Kieselgel-60, 70-230 mesh, n-hexane eluent) to give the product, tert-butyl trithioperbenzoate (21) as a dark purple oil in 60% yield. $^1$H-nmr (CDCl$_3$) d (ppm) 1.32 (s, 9H), 7.45 (m, 3H) and 8.00 (m, 2H).

Example 13

Preparation of 2-phenylprop-2-yl 4-chlorodithiobenzoate (22) (C, p=1, R=C(CH$_3$)$_2$Ph; Z=p-ClC$_6$H$_4$)

A mixture of 4-chlorodithiobenzoic acid (13 g) and a-methylstyrene (15 mL) were heated at 70° C. for 1 hour. To the reaction mixture was added n-hexane (30 mL) and heating was continued at 70° C. for 16 hours. The resultant mixture was reduced to a crude oil. Purification, of the oil by chromatography (aluminium oxide column (activity II-III) n-hexane eluent) gave the title compound (22) as a purple oil (8.5 g, 40%). $^1$H-nmr (CDCl$_3$) d (ppm) 2.00 (s, 6H); 7.30 (m, 5H); 7.55 (d, 2H) and 7.83 (d, 2H).

Example 14

Preparation of 2-phenylprop-2-yl 1-dithionaphthalate (23) (C, p=1, R=C(CH$_3$)$_2$Ph; Z=1-naphthyl)

The procedure was analogous to that used for the preparation of compound (5). The reaction of 1-(chloromethyl)naphthalene (17.6 g, 0.1 mol), sulfur (6.4 g, 0.2 mol) and sodium methoxide (25% solution in methanol, 46 mL) in methanol (50 mL) gave 1-dithionaphthoic acid (10 g, 49%). A mixture of 1-dithionaphthoic acid (10 g) and a-methylstyrene (10 mL) in carbon tetrachloride (20 mL) was heated at 70° C. for 16 hours. After removal of carbon tetrachloride and unreacted a-methylstyrene, the residue was chromatographed (Kieselgel-60, 70-230 mesh, 5% diethyl ether in n-hexane eluent) to yield 2-phenylprop-2-yl 1-dithionaphthalate (23) (9.2 g, 58%) as a dark red oil. $^1$H-nmr (CDCl$_3$) d (ppm) 2.06 (s, 6H); 7.29-7.55 (m, 7H); 7.66 (m, 2H); 7.85 (m, 2H) and 8.00 (m, 1H).

Example 15

Preparation of 4-cyanopentanoic acid dithiobenzoate (24) (C, p=1, R=C(CH$_3$)(CN)(CH$_2$)$_3$CO$_2$H; Z=Ph)

Compound (24) can be made by a procedure analogous to that used for preparation of compounds (14) and (15). m.p. 97-99° C. $^1$H-nmr(CDCl$_3$) δ (ppm) 1.95 (s, 3H); 2.40-2.80 (m, 4H); 7.42 (m, 2H); 7.60 (m, 1H) and 7.91 (m, 2H).

Example 16

Preparation of dibenzyl tetrathioterephthalate (25) (D, m=2, R=CH$_2$Ph; Z'=1,4-phenylene)

The sodium salt of tetrathioterephthalic acid was obtained from the reaction of a,a'-dibromo-p-xylene (6.6 g, 25 mmol), elemental sulfur (3.2 g, 0.1 mol), and sodium methoxide (25% in methanol, 24 mL, 0.1 mol) in methanol (30 mL) at 70° C. for 5 hours. The reaction mixture was evaporated to dryness and then dissolved in acetonitrile (50 mL). This was treated with benzyl chloride (6.3 g, 50 mmol) at room temperature for 16 hours. The suspension was filtered, the solid collected and extracted with chloroform/water. The organic extract was dried and reduced to give the title compound as a red solid (2.14 g, 21%). Melting point: 111-116° C. (dec.). $^1$H-nmr (CDCl$_3$) d (ppm) 4.60 (s, 4H), 7.30-7.45 (m, 10H) and 7.97 (s, 4H).

Procedure 10

Preparation of dibenzyl trithiocarbonate (26) (C, p=1, R=CH$_2$Ph; Z=SCH$_2$Ph)

The title compound was prepared according to the procedure described by Leung, M-K., et al, *J. Chem. Research (S)*, 478-479, (1995).

Procedure 11

Preparation of carboxymethyl dithiobenzoate (27) (C, p=1, R=CH$_2$COOH; Z=Ph)

The title compound was prepared according to the procedure of Jensen and Pedersen, *Acta Chem. Scand.*, 15, 1087-1096 (1961). $^1$H-nmr (CDCl$_3$) d (ppm) 4.24 (s, 2H), 7.43-8.00 (m, 5H) and 8.33 (s, 1H).

Example 17

Preparation of poly(ethylene oxide) with dithiobenzoate end group (28) (C, p=1, R=CH$_2$COO—(CH$_2$CH$_2$O)$_n$Me; Z=Ph)

A mixture of carboxymethyl dithiobenzoate (27) (0.5 g, 2.36 mmol), polyethylene glycol monomethyl ether (MWt. 750) (1.7 g, 2.36 mmol), anhydrous pyridine (2 mL), dicyclohexylcarbodiimide (1.46 g, 7.1 mmol) and 4-toluenesulfonic acid (10 mg) was stirred under nitrogen at 50° C. for 16 hours. The mixture was reduced in vacuo and the residue partitioned between chloroform (10 mL) and saturated aqueous sodium bicarbonate (2 mL). The organic phase was dried over anhydrous sodium sulfate and reduced to a red oil (quantitative yield based on 24). $^1$H-nmr (CDCl$_3$) d (ppm) 3.35 (s, 3H), 3.53 (br.t, 2H), 3.65 (s, 50H), 3.7 (br.t, 2H), 4.23 (s, 2H), 4.30 (br.t, 2H), 7.38 (t, 2H), 7.54 (t, 1H), 8.0 (d, 2H).

Example 18

Preparation of poly(ethylene oxide) with dithiobenzoate end group (29) (C, p=1, R=C(CH$_3$)(CN) CH$_2$CH$_2$)COO—(CH$_2$CH$_2$O)$_n$Me; Z=Ph)

A mixture of 4-cyano-4-(thiobenzoylthio)pentanoic acid (24) (0.23 g), polyethylene glycol monomethyl ether (1.8 g, MWt 750) and a catalytic amount of 4-(N,N-dimethylamino)pyridine in dichloromethane (5 mL) was added by a solution of dicyclohexylcarbodiimide (0.34 g) in dichloromethane (5 mL) at room temperature under nitrogen. The mixture was stirred for two hours and filtered to remove the dicyclohexylurea by-product. The fitrate was extracted with water seven times (7×10 mL), dried over anhydrous magnesium sulfate and reduced to a red waxy solid (quantitative yield based on 24). $^1$H-nmr (CDCl$_3$) d (ppm) 1.92 (s, 3H), 2.60-2.72 (m, 4H), 3.35 (s, 3H), 3.53 (m, 2H), 3.63 (s, 64H), 3.65 (m, 2H), 4.26 (t, 2H), 7.40 (t, 2H), 7.57 (t, 1H) and 7.91 (d, 2H).

The following Examples 19-88 represent non-limiting examples which demonstrate the operation of the process and the products obtainable thereby.

EXAMPLES 19 TO 88

General Experimental Conditions

In all instances, monomers were purified (to remove inhibitors) and flash-distilled immediately prior to use. The experiments referred to as controls were experiments run without the CTA unless otherwise specified. For polymerizations performed in ampoules, degassing was accomplished by repeated freeze-evacuate-thaw cycles. Once degassing was complete, the ampoules were flame sealed under vacuum and completely submerged in an oil bath at the specified temperature for the specified times. The percentage conversions were calculated gravimetrically unless otherwise indicated.

The structures of polymers and block copolymers have been verified by application of appropriate chromatographic and spectroscopic methods. Gel permeation chromatography (GPC) has been used to establish the molecular weight and molecular weight distribution (polydispersity) of the polymers. Unless otherwise specified, a Waters Associates liquid chromatograph equipped with differential refractometer and 10$^6$, 10$^5$, 10$^4$, 10$^3$, 500 and 100 Å Ultrastyragel columns was used. Tetrahydrofuran (flow rate of 1.0 mL/min) was used as eluent. The molecular weights are provided as polystyrene equivalents. The terms $M_n$, $M_w$ and $M_w/M_n$ are used to indicate the number and weight average molecular weights and the polydispersity respectively. Theoretical molecular weights [$M_n$ (calc)] were calculated according to the following expression:

$M_n$ (calc)=[monomer]/[CTA]×conversion×MWt of monomer

For low molecular weight polymers (degree of polymerization<50), the end group [ZC(=S)S—] can be determined by $^1$H NMR spectroscopy. In cases where the end group is (Aryl)C(=S)S— or (Alkyl)C(=S)S— the end groups can be observed in polymers with degree of polymerization $^\geq$1000 by UV-Visible spectrophotometry. Gel permeation chromatography coupled with UV-Visible spectrophotometry enables a measurement of the purity of block copolymers in these cases.

Example 19

Preparation of Low Polydispersity Poly(methyl Methacrylate) Using 2-phenylprop-2-yl Dithiobenzoate (5)

A stock solution containing methyl methacrylate (15 mL), azobisisobutyronitrile (20 mg) and 2-phenylprop-2-yl dithiobenzoate (5) (60.7 mg) in benzene (5 mL) was prepared. Aliquots (4 mL) were transferred to ampoules, degassed and sealed. The ampoules were heated at 60° C. for the times indicated in the Table.

TABLE 1

Molecular weight and conversion data for poly(methyl methacrylate) prepared with 2-phenylprop-2-yl dithiobenzoate (5) at 60° C.

| Entry | time/hr | $M_n$ | $M_w/M_n$ | % Conv. | $M_n$ (calc) |
|---|---|---|---|---|---|
| 1 | 2 | 9 800 | 1.27 | 13.5 | 8 410 |
| 2 | 4 | 18 000 | 1.19 | 27.3 | 17 000 |
| 3 | 8 | 29 800 | 1.15 | 51.5 | 32 100 |
| 4 | 16 | 56 200 | 1.12 | 95.0 | 59 200 |

Example 20

Preparation of Low Polydispersity Poly(methyl Acrylate) with 1-phenylethyl Dithiobenzoate (4)

Stock solutions (I) of azobisisobutyronitrile (6.6 mg) in benzene (50 mL) and (II) of 1-phenylethyl dithiobenzoate (4) (87.6 mg) in benzene (50 mL) were prepared. Aliquots of stock solution (I) (2 mL) and stock solution (II) (6 mL) were transferred to ampoules containing methyl acrylate (2 mL) which were degassed, sealed and heated at 60° C. for the times specified in Table 2 below.

TABLE 2

Molecular weight and conversion data for poly(methyl acrylate) prepared with 1-phenylethyl dithiobenzoate (4) at 60° C.

| Entry | time/hr | $M_n$ | $M_w/M_n$ | % Conv. |
|---|---|---|---|---|
| 1 | 20 | 13 500 | 1.11 | 26.2 |
| 2 | 64 | 28 800 | 1.13 | 52.9 |
| 3 | 110 | 32 700 | 1.16 | 63.8 |

Example 21

Preparation of Low Polydispersity Poly(n-butyl Acrylate) with 1-phenylethyl Dithiobenzoate (4)

A stock solution (I) of azobisisobutyronitrile (13.4 mg) in benzene (50 mL) and a stock solution (II) of 1-phenylethyl dithiobenzoate (4) (50.6 mg) in benzene (50 mL) were prepared. Aliquots of solution (I) (10 mL) and solution (II) (20 mL) were added to a reaction vessel containing n-butyl acrylate (20 mL). The reaction mixture was degassed, sealed and heated at 60° C. for 2 hours, to give poly(n-butyl acrylate) (2.48 g, 13.9% conversion) with $M_n$ 33,600, $M_w$ 37,800 and $M_w/M_n$ 1.13.

Example 22

Preparation of Low Polydispersity Poly(acrylic Acid) Using 1-phenylethyl Dithiobenzoate (4)

Stock solution (I) of azobisisobutyronitrile (6.64 mg) in N,N-dimethylformamide (DMF) (25 mL) and stock solution (II) of 1-phenylethyl dithiobenzoate (4) (17.7 mg) in DMF (25 mL) were prepared. Aliquots of stock solution (I) (2 mL), stock solution (II) (6 mL) and acrylic acid (2 mL) were placed in a reaction vessel. The reaction mixture was degassed, sealed and heated at 60° C. for 4 hours. After removal of the solvent and excess monomer, poly(acrylic acid) (0.37 g, 17.5% conversion) was obtained. A portion was methylated (tetramethylammonium hydroxide (25% in methanol) and excess methyl iodide) to give poly(methyl acrylate) of $M_n$ 13792, $M_w$ 16964 and $M_w/M_n$ 1.23.

Example 23

Preparation of Low Polydispersity Polystyrene via Bulk Polymerization of with Benzyl Dithiobenzoate (3)

A stock solution of styrene (60 mL) and azobisisobutyronitrile (16.9 mg) was prepared. Aliquots (5 mL) were removed and transferred to ampoules containing benzyl dithiobenzoate (11.4 mg). The ampoules were degassed, sealed and heated at 60° C. for the periods of time indicated in the Table below. The results are listed in Table 3 below.

TABLE 3

Molecular weight and conversion data for polystyrene prepared with benzyl dithiobenzoate at 60° C.

| Entry | time/hr | $M_n$ | $M_w/M_n$ | % Conv. |
|---|---|---|---|---|
| 1 (control) | 1 | 164 000 | 1.83 | 1.61 |
| 2 | 1 | 1 500 | 1.36 | 0.68 |
| 3 | 2 | 2 260 | 1.27 | 1.49 |
| 4 | 4 | 3 630 | 1.24 | 3.46 |
| 5 | 8 | 6 020 | 1.21 | 6.92 |
| 6 | 12 | 8 900 | 1.16 | 10.60 |
| 7 | 16 | 11 780 | 1.16 | 13.66 |
| 8 | 20 | 14 380 | 1.13 | 17.16 |
| 9 | 30 | 18 500 | 1.12 | 22.43 |
| 10 | 50 | 25 200 | 1.17 | 31.82 |
| 11 | 100 | 33 400 | 1.13 | 42.32 |

Example 24

Preparation of Low Polydispersity Polystyrene via Bulk Polymerization of Styrene Using 2-phenylprop-2-yl Dithiobenzoate (5)

Polystyrene was prepared under the conditions used for Example 5 with 2-phenylprop-2-yl dithiobenzoate (5) (11.4 mg per ampoule) in place of benzyl dithiobenzoate. Results are shown in Table 4 below.

TABLE 4

Molecular weight and conversion data for polystyrene prepared with 2-phenylprop-2-yl dithiobenzoate at 60° C.

| Entry | time/hr | $M_n$ | $M_w/M_n$ | % Conv. |
|---|---|---|---|---|
| 1 (control) | 1 | 285 000 | 1.63 | 1.67 |
| 2 | 1 | 833 | 1.12 | 0.49 |
| 3 | 4 | 4 510 | 1.09 | 3.74 |
| 4 | 20 | 21 500 | 1.14 | 19.45 |
| 5 | 50 | 40 000 | 1.17 | 37.49 |
| 6 | 100 | 52 000 | 1.18 | 57.33 |

Example 25

Preparation of Low Polydispersity Polystyrene via Thermal Polymerization of Styrene Using 1-phenylethyl Dithiobenzoate (4) at 100° C.

A stock solution of styrene (10 mL) and 1-phenylethyl dithiobenzoate (4) (24.8 mg) was prepared. Aliquots (2 mL) of this solution were transferred to ampoules which were degassed, sealed and heated at 100° C. for the times indicated in Table 5 below and analyzed by GPC.

TABLE 5

Molecular weight and conversion data for polystyrene prepared with 1-phenylethyl dithiobenzoate (4) at 100° C.

| Entry | time/hr | $M_n$ | $M_w$ | $M_w/M_n$ | % Conv. |
|---|---|---|---|---|---|
| 1 (Control) | 6 | 227 000 | 434 000 | 1.91 | 21.7 |
| 2 | 6 | 5 800 | 6 300 | 1.09 | 9.7 |
| 3 | 20 | 22 000 | 25 000 | 1.15 | 36.8 |
| 4 | 64 | 38 500 | 47 000 | 1.22 | 70.6 |
| 5 | 120 | 50 000 | 61 000 | 1.23 | 91.9 |

Example 26

Preparation of Low Polydispersity Polystyrene via Thermal Polymerization of Styrene Using 1-phenylethyl Dithiobenzoate (4) at 100° C.

Example 25 was repeated with a threefold higher concentration of 1-phenylethyl dithiobenzoate (4) (75.6 mg) in the stock solution. The results are summarized in the Table 6 below.

TABLE 6

Molecular weight and conversion data for polystyrene prepared with 1-phenylethyl dithiobenzoate (4) at 100° C.

| Entry | time/hr | $M_n$ | $M_w$ | $M_w/M_n$ | % Conv. |
|---|---|---|---|---|---|
| 1 | 6 | 3 440 | 37 30 | 1.08 | 12.3 |
| 2 | 20 | 10 000 | 11 000 | 1.08 | 35.0 |
| 3 | 64.5 | 22 000 | 24 000 | 1.10 | 65.6 |
| 4 | 120 | 27 000 | 31 000 | 1.16 | 87.6 |

Example 27

Preparation of Low Polydispersity Polystyrene via Thermal Polymerizations of Styrene Using 2-phenylprop-2-yl Dithiobenzoate (5) at 100° C.

Example 26 was repeated with 2-phenylprop-2-yl dithiobenzoate (5) in place of 1-phenylethyl dithiobenzoate (4) (same molar concentration). The results are listed in Table 7.

TABLE 7

Molecular weight and conversion data for polystyrene prepared with 2-phenylprop-2-yl dithiobenzoate (5) at 100° C.

| Entry | time/hr | $M_n$ | $M_w$ | $M_w/M_n$ | % Conv. |
|---|---|---|---|---|---|
| 1 | 2 | 1 520 | 1 690 | 1.12 | 4.3 |
| 2 | 6 | 5 680 | 6 140 | 1.08 | 14.3 |
| 3 | 20 | 13 800 | 14 900 | 1.08 | 39.9 |
| 4 | 64 | 25 000 | 28 100 | 1.12 | 81.0 |
| 5 | 119 | 26 000 | 30 000 | 1.14 | 88.0 |

Example 28

Preparation of Low Polydispersity Polystyrene via Emulsion Polymerization of Styrene Using Benzyl Dithiobenzoate (3) at 80° C.

A 5-neck reaction vessel fitted with a stirrer, condenser and thermocouple was charged with water (75 g) and sodium dodecyl sulfate (5 g of 10% aqueous solution). The mixture was degassed under nitrogen at 80_C for 40 minutes. A solution of 4,4'-azobis(4-cyanopentanoic acid) (0.14 g) and benzyl dithiobenzoate (3) (0.215 g) in styrene (3.7 g) was added as a single shot. Further 4,4'-azobis(4-cyanopentanoic acid) (0.209 g) in sodium dodecyl sulfate (1% aq solution) (24 g) at a rate of 0.089 mL/min along with styrene (32.9 g) at a rate of 0.2 mL/min were added by syringe pumps. On completion of the initiator feed, the reaction was held at 80_C. for a further 90 minutes. The isolated polystyrene had $M_n$ 53 200; $M_w/M_n$ 1.37 at 73% conversion.

Example 29

Preparation of Low Polydispersity Polystyrene via Emulsion Polymerizations of Styrene Using Benzyl Dithiobenzoate (3) at 80° C.

Example 28 was repeated with a higher concentration of benzyl dithiobenzoate (3) (0.854 g).

The isolated polystyrene had $M_n$ 3 010; $M_w/M_n$ 1.20 at 19% conversion.

Example 30

Preparation of Low Polydispersity Poly(methyl Acrylate-block-ethyl Acrylate)

A sample of poly(methyl acrylate) (0.17 g, $M_n$ 24 070, $M_w/M_n$ 1.07) made with 1-phenylethyl dithiobenzoate (4) (as described in Example 20) was dissolved in ethyl acrylate (2 mL) and benzene (8 mL) containing azobisisobutyronitrile (0.52 mg). The vessel was degassed, sealed and heated at 60° C. for 2 hours to give poly(methyl-acrylate-block-ethyl acrylate) (0.22 g, 10.8% conversion), $M_n$ 30 900, $M_w/M_n$ 1.10.

Example 31

Preparation of Low Polydispersity Poly(n-butyl Acrylate-block-acrylic Acid)

A stock solution of azobisisobutyronitrile (6.64 mg) in DMF (25 mL) was prepared. In an ampoule, poly(n-butyl acrylate) from Example 21, (0.5 g, $M_n$ 33569, $M_w/M_n$ 1.13) was dissolved in DMF (5.5 mL), acrylic acid (4 mL) and stock solution (0.5 mL). The mixture was degassed, sealed and heated at 60° C. for 2 hours. After removal of the solvent and unreacted monomer, poly(n-butyl acrylate-block-acrylic acid) was obtained (0.848 g, 8.3% conversion). GPC results (after methylation of the acrylic acid of the diblock): $M_n$ 52 427; $M_w$ 63 342; $M_w/M_n$ 1.19.

Example 32

Preparation of Low Polydispersity Polystyrene Using Benzyl Dithioacetate (12)

A stock solution of styrene (10 mL), benzyl dithioacetate (12) (17 mg) and azobisisobutyronitrile (2.8 mg) was prepared. Aliquots (2 mL) were removed and transferred to ampoules. The ampoules were degassed, sealed and heated at 60° C. for the periods of time indicated in Table 8 below.

TABLE 8

Molecular weight and conversion data for polystyrene prepared with benzyl dithioacetate(12) at 60° C.

| Entry | time/hr | $M_n$ | $M_w$ | $M_w/M_n$ | % Conv. |
|---|---|---|---|---|---|
| 1 | 2 | 6 840 | 11 800 | 1.72 | 1.8 |
| 2 | 4 | 8 570 | 13 500 | 1.58 | 5.0 |
| 3 | 16 | 19 000 | 25 000 | 1.32 | 16.5 |
| 4 | 40 | 30 000 | 37 000 | 1.24 | 28.9 |

Example 33

Preparation of Low Polydispersity Poly(n-butyl Acrylate) Using Benzyl Dithiobenzoate (3)

Stock solution (I) of azobisisobutyronitrile (13.4 mg) in benzene (50 mL) and stock solution (II) of benzyl dithiobenzoate (3) (9.62 mg) in benzene (10 mL) were prepared.

Aliquots of stock solution (I) (2 mL) and stock solution (II) (4 mL) were transferred to ampoules already containing n-butyl acrylate (4 mL). The ampoules were degassed, sealed and heated at 60° C. for the periods of time indicated in Table 9 below.

TABLE 9

Molecular weight and conversion data for poly(n-butyl acrylate) prepared with benzyl dithiobenzoate (3) at 60° C.

| Entry | time/hr | $M_n$ | $M_w/M_n$ | $M_n$ (calc) | % Conv. |
|---|---|---|---|---|---|
| 1 | 2 | 26 000 | 1.12 | 25 866 | 11.4 |
| 2 | 8 | 92 000 | 1.14 | 90 760 | 40.0 |

Example 34

Preparation of Low Polydispersity Poly(N,N-dimethyl Acrylamide) Using Benzyl Dithiobenzoate (3)

A stock solution (I) of azobisisobutyronitrile (2.5 mg) and N,N-dimethylacrylamide (10 mL) in benzene (50 mL) was prepared. Stock solution (II) containing benzyl dithiobenzoate (3) (4 mg) in stock solution (I) (20 mL) was prepared. Aliquots of stock solutions (I) and (II) were transferred to ampoules (in the quantities indicated in the Table below). The ampoules were degassed, sealed and heated at 60° C. for 1 hour. The molecular weight and polydispersity data are summarised in Table 10 below.

TABLE 10

Molecular weight and conversion data for poly(N,N-dimethyl acrylamide) prepared with benzyl dithiobenzoate (3) at 60° C.

| Entry | Solution (I) (mL) | Solution (II) (mL) | CTA (mg) | $M_n$ | $M_w/M_n$ | $M_n$ (calc) | % Conv. |
|---|---|---|---|---|---|---|---|
| 1 | 0 | 10 | 2 | 35 000 | 1.14 | 30 266 | 12.9 |
| 2 | 5 | 5 | 1 | 135 000 | 1.23 | 120 597 | 25.7 |
| 3 | 7.5 | 2.5 | 0.5 | 224 000 | 1.44 | 293 742 | 31.3 |
| 4 (control) | 10 | 0 | 0 | 833 000 | 2.59 | — | 76.9 |

Example 35

Emulsion Polymerization of Styrene in the Presence of Benzyl Dithioacetate at 80° C. with Sodium Dodecyl Sulfate as Surfactant and 4,4'-azobis(4-cyanopentanoic Acid) as Initiator A 5-neck reaction vessel fitted with a stirrer, condenser and thermocouple was charged with water (75 g) and sodium dodecyl sulfate (5 g of 10% aqueous solution). The mixture was degassed under nitrogen at 80_C for 40 minutes. A solution of 4,4'-azobis(4-cyanopentanoic acid) (0.14 g) and benzyl dithioacetate (0.155 g) in styrene (3.7 g) was added as a single shot. Further 4,4'-azobis(4-cyanopentanoic acid) (0.211 g) in sodium dodecyl sulfate (1% aq solution) (24 g) was added at a rate of 0.089 mL/min along with styrene (32.9 g) at a rate of 0.2 mL/min.

On completion of the initiator feed, the reaction was held at 80_C for a further 90 minutes. The results of the experiment are summarized in Table 11.

TABLE 11

Molecular weight and conversion data for polystyrene prepared with benzyl dithioacetate in emulsion at 80° C.

| Entry | Reaction time/min | $M_n$ | $M_w/M_n$ | % Conversion[a] |
|---|---|---|---|---|
| 1 | 75 | 21 000 | 1.27 | 97[a] |
| 2 | 120 | 29 000 | 1.26 | 98[a] |
| 3 | 180 | 35 000 | 1.33 | >99 |
| 4 | 240 | 37 000 | 1.35 | >99 |
| 5 | 270 | 38 000 | 1.34 | >99 |
| 6 | 360 | 36 000 | 1.38 | >99 |

[a]Instantaneous conversion (conversion of monomer added up to time of sampling).

Example 36

Preparation of Narrow Polydispersity Poly(styrene-block-N,N-dimethylacrylamide)

The polystyrene ($M_n$ 20300, $M_{w/Mn}$ 1.15) used in this experiment was prepared by bulk polymerization of styrene (100 mL) at 60° C. for 30.5 hours with azobisisobutyronitrile (28.17 mg) as initiator in the presence of benzyl dithiobenzoate (3) (228 mg).

A solution of the above polystyrene (0.2 g), N,N-dimethylacrylamide (2 mL), azobisisobutyronitrile (0.5 mg) and benzene (8 mL) was transferred to an ampoule. The resulting mixture was degassed, sealed and heated at 60° C. for 1 hour. The volatiles were removed in vacuo to give poly(styrene-block-dimethylacrylamide) at 0.4 g, 10.4% conversion, with $M_n$ 43 000 and $M_w/M_n$ 1.24.

Example 37

Preparation of Low Polydispersity Poly(4-methylstyrene-block-styrene)

A mixture of polystyrene (0.5 g, $M_n$ 20300, $M_w/M_n$ 1.15, prepared as described in Example 36), 4-methylstyrene (2 mL), azobisisobutyronitrile (2.5 mg) and benzene (0.5 mL) were transferred to an ampoule. The resulting mixture was degassed, sealed and heated at 60° C. for 3 hours. Volatiles were removed under reduced pressure to give poly(styrene-block-4-methylstyrene) (0.81 g, 17.1% conversion, $M_n$ 25 400 and $M_w/M_n$ 1.19).

Example 38

Preparation of Low Polydispersity Poly(methyl Methacrylate-block-styrene)

Poly(methyl methacrylate) ($M_n$ 17408, $M_w/M_n$ 1.20) was prepared under the conditions described for Example 19 with a reaction time of 4 h. This polymer (1.7 g) was dissolved in ethyl acetate and the solution transferred to an ampoule. The ethyl acetate was removed under reduced pressure and azobisisobutyronitrile (2.82 mg) and styrene (10 mL) were added. The ampoule was degassed, sealed and heated at 60° C. for 20 hours. After removal of the unreacted styrene, poly(methyl methacrylate-block-styrene) was obtained (3.9 g, 23.5% conversion) with $M_n$ 35 000; $M_w$ 44 000; $M_w/M_n$ 1.24.

Example 39

Preparation of Low Polydispersity Poly(n-butyl Acrylate) via the Solution Polymerization of n-butyl Acrylate at 90° C. in the Presence of 1,4-bis(thiobenzoylthiomethyl)benzene (8)

A stock solution of 1,1'-azobis(1-cyclohexanecarbonitrile) (8.03 mg) in benzene (10 mL) was prepared. Aliquots (1 mL) of the stock solution were added to ampoules containing n-butyl acrylate (4 mL), 1,4-bis-(thiobenzoylthiomethyl)benzene (8) (12.7 mg) and benzene (5 mL). The contents of the ampoules were degassed, sealed and heated at 90° C. for the times given in Table 12 below.

TABLE 12

Molecular weight and conversion data for poly(n-butyl acrylate)prepared with 1,4-bis(thiobenzoylthiomethyl)benzene (8) at 90° C.

| Entry | time/hr | $M_n$ | $M_w/M_n$ | $M_n$ (calc) | % Conv. |
|---|---|---|---|---|---|
| 1 | 1 | 5 090 | 1.21 | 5 079 | 4.4 |
| 2 | 5 | 57 000 | 1.32 | 65 571 | 56.8 |

Example 40

Preparation of Low Polydispersity Poly(n-butyl acrylate) via the Solution Polymerization of n-butyl Acrylate at 90° C. in the Presence of 1,4-bis(2-thiobenzoylthioprop-2-yl)benzene (10)

Stock solution (I) of 1,1'-azobis(1-cyclohexanecarbonitrile) (10.09 mg) in benzene (25 mL), and stock solution (II) of 1,4-bis(2-thiobenzoylthioprop-2-yl)benzene (10) (175.1 mg) in benzene (25 mL) were prepared. Aliquots of stock solution (I) (2 mL) and stock solution (II) (4 mL) were added to ampoules containing n-butyl acrylate (4 mL). The ampoules were degassed, sealed and heated at 90° C. for the times shown in Table 13 below.

TABLE 13

Molecular weight and conversion data for poly(n-butyl acrylate)prepared with 1,4-bis(2-thiobenzoylthioprop-2-yl)benzene (10) at 90° C.

| Entry | time/hr | $M_n$ | $M_w/M_n$ | $M_n$ (calc) | % Conv. |
|---|---|---|---|---|---|
| 1 | 5 | 937 | 1.13 | 952 | 1.6 |
| 2 | 16 | 28 000 | 1.21[a] | 27 365 | 46.0 |
| 3 | 42 | 41 000 | 1.37[a] | 43 904 | 73.8 |

[a]trimodal molecular weight distribution

Example 41

Preparation of Low Polydispersity Star Polystyrene via the Thermal Polymerization of Styrene at 100° C. in the Presence of Hexakis(thiobenzoylthiomethyl)benzene (7)

A stock solution comprising of styrene (10 mL) and hexakis(thiobenzoylthiomethyl)benzene (7) (48.9 mg) was prepared. Aliquots of the stock solution (2 mL) were transferred to ampoules which were degassed, sealed and heated at 100° C. for the times given in Table 14 below.

TABLE 14

Molecular weight and conversion data for star polystyrene prepared with hexakis(thiobenzoylthiomethyl)benzene (7) at 100° C.

| Entry | time/hr | $M_n$ | $M_w$ | $M_w/M_n$ | % Conv. |
|---|---|---|---|---|---|
| 1 | 6 | 1 350 | 1 530 | 1.13 | 0.33 |
| 2 | 20 | 34 100 | 46 500 | 1.36 | 27.5 |
| 3 | 64 | 80 000 | 133 000 | 1.67 | 72.1 |

Example 42

Preparation of Low Polydispersity Star Polystyrene via the Thermal Polymerization of Styrene at 100° C. in the Presence of 1,2,4,5-tetrakis-(thiobenzoylthiomethyl)benzene (9)

A stock solution of styrene (10 mL) and 1,2,4,5-tetrakis (thiobenzoylthiomethyl)benzene (9) (54.5 mg) was prepared. Aliquots (2 mL) of the stock solution were transferred to ampoules which were degassed, sealed and heated at 100° C. for the times given in the Table below. Polymer was obtained by removal of the volatiles. The results are summarized in Table 15 below.

TABLE 15

Molecular weight and conversion data for star polystyrene prepared with 1,2,4,5-tetrakis(thiobenzoylthiomethyl)benzene (9) at 100° C.

| Entry | time/hr | $M_n$ | $M_w$ | $M_w/M_n$ | $M_n$ (calc) | % Conv. |
|---|---|---|---|---|---|---|
| 1 | 6 | 989 | 1 100 | 1.11 | — | 0.88 |
| 2 | 20 | 26 000 | 31 100 | 1.20 | 27 257 | 22.0 |
| 3 | 64 | 67 500 | 87 600 | 1.30 | 90 814 | 73.3 |

Example 43

Preparation of Low Polydispersity Star Polystyrene via the Thermal Polymerization of Styrene at 120° C. in the Presence of 1,2,4,5-tetrakis-(thiobenzoylthiomethyl)benzene (9)

A stock solution of styrene (10 mL) and 1,2,4,5-tetrakis (thiobenzoylthiomethyl)benzene (9) (54.5 mg) was prepared. Aliquots (2 mL) of the stock solution were transferred to ampoules which were degassed, sealed and then heated at 120° C. for the times given below. The polymer was isolated by removal of the volatiles. The results are summarized in Table 16 below.

TABLE 16

Molecular weight and conversion data for star polystyrene prepared with 1,2,4,5-tetrakis(thiobenzoylthiomethyl)benzene (9) at 120° C.

| Entry | time/hr | $M_n$ | $M_w$ | $M_w/M_n$ | $M_n$ (calc) | % Conv. |
|---|---|---|---|---|---|---|
| 1 | 6 | 43 000 | 55 000 | 1.29 | 51416 | 41.5 |
| 2 | 20 | 75 000 | 109 000 | 1.44 | 100353 | 81.0 |
| 3 | 64 | 80 000 | 119 000 | 1.49 | 109770 | 88.6 |

Example 44

Preparation of Low Polydispersity Poly(methyl Methacrylate) Using 2-(ethoxycarbonyl)prop-2-yl Dithiobenzoate (14)

The method of Example 19 was used with 2-(ethoxycarbonyl)prop-2-yl dithiobenzoate (14) (same molar concentrations). Results are summarized in Table 17 below.

TABLE 17

Molecular weight and conversion data for poly(methyl methacrylate) prepared with 2-(ethoxycarbonyl)prop-2-yl dithiobenzoate (14) at 60° C.

| Entry | time/hr | $M_n$ | $M_w/M_n$ | % Conv. |
|---|---|---|---|---|
| 1 | 2 | 30 000 | 1.89 | 22.7 |
| 2 | 4 | 35 000 | 1.72 | 37.1 |
| 3 | 8 | 40 000 | 1.66 | 67.4 |
| 4 | 16 | 53 000 | 1.48 | >95 |

Example 45

Preparation of Low Polydispersity Poly(methyl methacrylate) with 2-cyanoprop-2-yl Dithiobenzoate (15)

The method of Example 19 was used with 2-cyanoprop-2-yl dithiobenzoate (15) (same molar concentrations). Results are summarized in Table 18 below.

TABLE 18

Molecular weight and conversion data for poly(methyl methacrylate) prepared with 2-cyanoprop-2-yl dithiobenzoate (15) at 60° C.

| Entry | time/hr | $M_n$ | $M_w/M_n$ | % Conv. |
|---|---|---|---|---|
| 1 | 2 | 9 200 | 1.26 | 16.2 |
| 2 | 4 | 17 000 | 1.19 | 39.4 |

TABLE 18-continued

Molecular weight and conversion data for poly(methyl methacrylate) prepared with 2-cyanoprop-2-yl dithiobenzoate (15) at 60° C.

| Entry | time/hr | $M_n$ | $M_w/M_n$ | % Conv. |
|---|---|---|---|---|
| 3 | 8 | 30 000 | 1.17 | 68.6 |
| 4 | 16 | 52 000 | 1.16 | >90 |

Example 46

Preparation of Low Polydispersity Poly(methyl methacrylate) Using 2-(4-chlorophenyl)prop-2-yl Dithiobenzoate (18)

The experimental conditions described in Example 19 (same molar concentrations) were used to prepare low polydispersity poly(methyl methacrylate) with 2-(4-chlorophenyl)prop-2-yl dithiobenzoate (18). Results are summarized in Table 19 below.

TABLE 19

Molecular weight and conversion data for poly(methyl methacrylate) prepared with 2-(4-chlorophenyl)propyl dithiobenzoate (18) at 60° C.

| Entry | time/hr | $M_n$ | $M_w/M_n$ | % Conv. | $M_n$ (calc) |
|---|---|---|---|---|---|
| 1 | 2 | 8 840 | 1.25 | 15.1 | 9 390 |
| 2 | 4 | 16 200 | 1.17 | 31.0 | 19 330 |
| 3 | 8 | 30 400 | 1.13 | 63.3 | 39 260 |
| 4 | 16 | 52 800 | 1.14 | >95 | 59 205 |

Example 47

Preparation of Low Polydispersity Poly(methyl Methacrylate) with Tert-butyl Trithioperbenzoate (21)

The experimental conditions described in Example 19 (same molar concentrations) were used to prepare low polydispersity poly(methyl methacrylate) with tert-butyl trithioperbenzoate (21). After heating at 60° C. for 16 hours, poly(methyl methacrylate) was obtained (62.8% conversion; Mn 92 000; $M_w/M_n$ 1.34).

Example 48

Preparation of Low Polydispersity Poly(methyl Methacrylate) with 2-phenylprop-2-yl 4-chlorodithiobenzoate (22)

The experimental conditions described in Example 19 (same molar concentrations) were used to prepare low polydispersity poly(methyl methacrylate) with 2-phenylprop-2-yl 4-chlorodithiobenzoate (22). After heating at 60° C. for 16 hours, poly(methyl methacrylate) was obtained (95% conversion; Mn 55 000; $M_w/M_n$ 1.07).

Example 49

Preparation of Low Polydispersity Poly(methyl Methacrylate) with 2-phenylprop-2-yl 1-dithionaphthalate (23)

The experimental conditions described in Example 19 (same molar concentrations) were used to prepare low polydispersity poly(methyl methacrylate) with 2-phenylprop-2-yl 1-dithionaphthalate (23). After heating at 60° C. for 16 hours, poly(methyl methacrylate) was obtained (95% conversion; Mn 57500; $M_w/M_n$ 1.10).

Example 50

Preparation of Low Polydispersity Poly(methyl Methacrylate) in Presence of 2-phenylprop-2-yl Dithiobenzoate (5) with Benzoyl Peroxide as Initiator A stock solution containing methyl methacrylate (20 mL), benzoyl peroxide (24.2 mg) and benzene (5 mL) was prepared. An aliquot (5 mL) of the stock solution was removed and 4 mL of this was placed in an ampoule labelled as control run (entry 1). 2-phenylprop-2-yl dithiobenzoate (5) (54.5 mg) was added to the remaining 20 mL of stock solution. Aliquots of this solution (4 mL) were transferred to four ampoules which were degassed, sealed and heated at 60_C. The results are summarized in Table 20 below.

TABLE 20

Molecular weight and conversion data for poly(methyl methacrylate) prepared with 2-phenylprop-2-yl dithiobenzoate (5) at 60° C.

| Entry | time/hr | $M_n$ | $M_w/M_n$ | % Conv. |
|---|---|---|---|---|
| 1 (control) | 2 | 453 000 | 1.81 | 11.1 |
| 2 | 2 | 6 080 | 1.40 | 6.8 |
| 3 | 4 | 10 300 | 1.28 | 14.8 |
| 4 | 8 | 20 000 | 1.17 | 33.4 |
| 5 | 16 | 41 000 | 1.13 | 77.9 |

The following example shows that polymerizations can be successfully carried out in both polar and nonpolar solvents.

Example 51

Preparation of Low Molecular Weight and Low Polydispersity Poly(methyl methacrylate) using 2-phenylprop-2-yl Dithiobenzoate (5) in Solvents such as Benzene or 2-butanone (MEK)

Stock solutions were prepared by adding methyl methacrylate (15 mL) and azobisisobutyronitrile (100 mg) to the required solvent (5 mL). Aliquots (10 mL) of each stock solution and appropriate amount of 2-phenylprop-2-yl dithiobenzoate (5) (see Table 23) were transferred to ampoules which were degassed and heated at 60° C. for specified times. Results are summarized in Table 21 below.

TABLE 21

Molecular weight and conversion data for poly(methyl methacrylate) prepared with 2-phenylprop-2-yl dithiobenzoate (5) at 60° C. in various solvents

| Dithioester (g) | Time (hr) | Solvent | $M_n$ | $M_w/M_n$ | % Conv. |
|---|---|---|---|---|---|
| 1.00 | 63.58 | Benzene | 3 200 | 1.17 | 79.8 |
| 0.40 | 24 | Benzene | 6 600 | 1.21 | 95.0 |
| 1.00 | 63.58 | 2-butanone | 2 800 | 1.17 | 61.3 |
| 0.40 | 24 | 2-butanone | 6 300 | 1.19 | 90.2 |

Example 52

Solution Polymerization of Methyl Methacrylate (25%) with 2-phenylprop-2-yl Dithiobenzoate (5)

A series of methyl methacrylate polymerizations were carried out with 2-phenylprop-2-yl dithiobenzoate (5). The results (see Table 24) when compared with control experiments clearly indicate that in the presence of dithioester there is some retardation (conversions are ca. 10% less for the same reaction time). A stock solution containing methyl methacrylate (10 mL), benzene (30 mL) and azobisisobutyronitrile (40 mg) was prepared. The stock solution was divided into two 20 mL portions. The first 20 mL portion was used for the 'control' experiments (entries 1-4). 2-phenylprop-2-yl dithiobenzoate (5) (100 mg) was added to the second 20 mL portion (entries 5-8). Aliquots (4 mL) of these solutions were transferred to ampoules which were degassed, sealed and heated at 60° C. for the specified period of time.

Results are summarized in Table 22 below.

TABLE 22

Molecular weight and conversion data for poly(methyl methacrylate) prepared with 2-phenylprop-2-yl dithiobenzoate (5) at 60° C. in benzene

| Entry | time/hr | parameter | control (no CTA) | with CTA (5) |
|---|---|---|---|---|
| 1 | 2 | $M_n$ | 98400 | 2880 |
|  |  | $M_w/M_n$ | 1.83 | 1.31 |
|  |  | % Conv. | 20.3 | 10.7 |
| 2 | 4 | $M_n$ | 88500 | 4570 |
|  |  | $M_w/M_n$ | 1.84 | 1.24 |
|  |  | % Conv. | 35.3 | 23.5 |
| 3 | 16 | $M_n$ | 69800 | 9250 |
|  |  | $M_w/M_n$ | 1.86 | 1.29 |
|  |  | % Conv. | 82.3 | 71.6 |
| 4 | 30 | $M_n$ | 58400 | 11720 |
|  |  | $M_w/M_n$ | 1.91 | 1.25 |
|  |  | % Conv. | 95.0 | 88.7 |

Example 53

Preparation of Low Polydispersity Polystyrene via Bulk Polymerization of Styrene Using 2-(ethoxycarbonyl)prop-2-yl Dithiobenzoate (14)

A stock solution of azobisisobutyronitrile (14.08 mg) in styrene (50 mL) was prepared. Aliquots (5 mL) of the stock solution were transferred to ampoules containing 2-(ethoxycarbonyl)prop-2-yl dithiobenzoate (14) (11.26 mg) which were degassed and sealed under vacuum. The ampoules were heated at 60° C. for periods of time indicated in Table 23 below.

TABLE 23

Molecular weight and conversion data for polystyrene prepared with 2-(ethoxycarbonyl)prop-2-yl dithiobenzoate (14) at 60° C.

| Entry | time/hr | $M_n$ | $M_w/M_n$ | % Conv. |
|---|---|---|---|---|
| 1 | 2 | 1 630 | 1.13 | 1.90 |
| 2 | 4 | 3 500 | 1.12 | 4.02 |
| 3 | 20 | 24 200 | 1.15 | 26.35 |

Example 54

Preparation of Low Polydispersity Polystyrene via Bulk Polymerization of Styrene Using 2,4,4-trimethylpent-2-yl Dithiobenzoate (17)

Example 53 was repeated with the exception that the dithioester used was 2,4,4-trimethylpent dithiobenzoate (17) (same molar concentrations). The results are summarized in Table 24 below.

TABLE 24

Molecular weight and conversion data for polystyrene prepared with 2,4,4-trimethylpent-2-yl dithiobenzoate (17) at 60° C.

| Entry | time/hr | $M_n$ | $M_w/M_n$ | % Conv. |
|---|---|---|---|---|
| 1 | 2 | 495 | 1.13 | 0.57 |
| 2 | 4 | 1 180 | 1.14 | 1.28 |
| 3 | 20 | 17 400 | 1.19 | 18.55 |

Example 55

Preparation of Low Polydispersity Polystyrene via Thermal Polymerization of Styrene with S-benzyl Diethoxyphosphinyldithioformate (20)

A stock solution of styrene (10 mL) and S-benzyl diethoxyphosphinyldithioformate (20) (30.9 mg) was prepared. Aliquots (2 mL) of the stock solution were transferred to ampoules which were degassed and sealed. The first three ampoules (Table 25, entries 1-3), were heated at 100° C. and the final ampoule (Table 25, entry 4), was heated at 120° C. Samples were removed at the time intervals indicated in the Table below and analyzed by GPC. The molecular weight increased linearly with % conversion and narrow. polydispersities are maintained throughout the polymerization.

TABLE 25

Molecular weight and conversion data for polystyrene prepared with benzyldiethoxyphosphinyldithioformate (20) at 100° C.

| Entry | Time/hr | $M_n$ | $M_w/M_n$ | % Conv. |
|---|---|---|---|---|
| 1[a] | 6 | 15 900 | 1.11 | 12.1 |
| 2[a] | 20 | 46 100 | 1.13 | 38.0 |
| 3[a] | 64 | 79 300 | 1.25 | 77.8 |
| 4[b] | 22 | 73 500 | 1.37 | 88.9 |

[a]Entries 1–3: The polymerizations were conducted at 100° C.
[b]Entry 4: The polymerization was conducted at 120° C.

Example 56

Preparation of Low Polydispersity Polystyrene via Thermal Polymerization of Styrene at 110° C. with 2-phenylprop-2-yl Dithiobenzoate (5)

Example 27 was repeated with the exception that the reaction temperature used was 110° C. instead of 100° C. After 16 hours at 110° C., polystyrene (55% conversion) with $M_n$ 14 400 and $M_w/M_n$ 1.04 was obtained.

The following two Examples demonstrate the use of the invention to prepare polymers with functional end groups (e.g. carboxylic acid).

Example 57

Preparation of Low Polydispersity Polystyrene via Thermal Polymerization of Styrene with Carboxymethyl Dithiobenzoate (27)

A stock solution of styrene (2 mL) and carboxymethyl dithiobenzoate (27) (24.8 mg) was prepared. Aliquots (1 mL) were transferred to two ampoules which were degassed, sealed and heated at 100° C. The results are summarized in Table 26 below.

TABLE 26

Molecular weight and conversion data for polystyrene prepared with carboxymethyl dithiobenzoate (27) at 100° C.

| Entry | time/hr | $M_n$ | $M_w/M_n$ | % Conv. |
|---|---|---|---|---|
| 1 | 6 | 3 900 | 1.49 | 11.4 |
| 2 | 64 | 7 400 | 1.34 | 42.5 |

Example 58

Preparation of Low Polydispersity Polystyrene via Thermal Polymerization of Styrene with 4-cyano-4-(thiobenzoylthio)pentanoic Acid (24)

A stock solution of styrene (2 mL) and 4cyano-4-(thiobenzoylthio)pentanoic acid (24) (32.8 mg) was prepared. Aliquots (1 mL) were transferred to two ampoules which were degassed, sealed and heated at 100° C. The $^{13}$C-nmr spectrum of the isolated polymer ($M_n$ 2,500; $M_w/M_n$ 1.05) had a signal at d 177.7 ppm indicating the presence of carboxy end-group at one end of the polystyrene. In addition, evidence from both $^1$H-nmr and $^{13}$C-nmr spectra indicate the presence of thiobenzoylthio end group. The results are summarized in Table 27 below.

TABLE 27

Molecular weight and conversion data for polystyrene prepared with 4-cyano-4-(thiobenzoylthio)pentanoic acid (24) at 100° C.

| Entry | time/hr | $M_n$ | $M_w/M_n$ | % Conv. |
|---|---|---|---|---|
| 1 | 6 | 2 500 | 1.05 | 19.7 |
| 2 | 64 | 8 900 | 1.05 | 61.3 |

Example 59

Preparation of Low Polydispersity Polystyrene via Thermal Polymerization of Styrene with Dibenzyl Trithiocarbonate (26)

A stock solution comprising of styrene (5 g) and dibenzyl trithiocarbonate (26) (43 mg) was prepared. Aliquots of the stock solution (2 g) were transferred to two ampoules which were degassed, sealed, and heated at 110° C. The results are summarized in Table 28 below.

TABLE 28

Molecular weight and conversion data for polystyrene prepared with dibenzyl trithiocarbonate (26) at 110° C.

| Entry | time/hr | $M_n$ | $M_w/M_n$ | % Conv. |
|---|---|---|---|---|
| 1 | 6 | 11,000 | 1.21 | 54 |
| 2 | 16 | 17,000 | 1.15 | 81 |

Example 60

Preparation of Low Polydispersity Poly(n-butyl Acrylate) Using Tert-butyl Trithioperbenzoate (21)

Stock solution (I) of azobisisobutyronitrile (13.4 mg) in benzene (50 mL) and stock solution (II) of tert-butyl trithioperbenzoate (21) (23.8 mg) in benzene (25 mL) were prepared.

Aliquots of stock solution (I) (2 mL) and stock solution (II) (4 mL) were transferred to ampoules containing n-butyl acrylate (4 mL). The ampoules were degassed, sealed and heated at 60° C. for the times indicated in the Table 29 which also shows the results of the polymer produced.

TABLE 29

Molecular weight and conversion data for poly(n-butyl acrylate) prepared with tert-butyl trithiophenylperformate (21) at 60° C.

| Entry | time/hr | $M_n$ | $M_w/M_n$ | % Conv. |
|---|---|---|---|---|
| 1 | 2 | 12 700 | 1.12 | 6.8 |
| 2 | 8 | 78 000 | 1.07 | 40.5 |
| 3 | 16 | 118 000 | 1.14[a] | 61.2 |
| 4 | 40 | 174 000 | 1.24[a] | 81.7 |

[a]Bimodal molecular weight distribution, with a small high molecular weight shoulder.

Example 61

Preparation of Low Polydispersity Poly(N,N-dimethylaminoethyl Methacrylate) Using 2-phenylprop-2-yl Dithiobenzoate (5)

Stock solution (I) of azobisisobutyronitrile (20 mg) and N,N-dimethylaminoethyl methacrylate (15 mL) in benzene (5 mL) and stock solution (II) consisting of stock solution (I) (18 mL) and 2-phenylprop-2-yl dithiobenzoate (5) (61.1 mg) were prepared. The remainder of stock solution (I) (2 mL) was used for the control experiment. Aliquots of stock solution (II) (4 mL) were transferred to ampoules and degassed, sealed and heated at 60° C. for the times indicated in Table 30.

TABLE 30

Molecular weight and conversion data for poly(N,N-dimethylaminoethyl methacrylate) prepared with 2-phenylprop-2-yl dithiobenzoate (5) at 60° C.

| Entry | time/hr | $M_n$ | $M_w/M_n$ | % Conv. |
|---|---|---|---|---|
| 1 (Control) | 2 | 13 000 | 40.2[a] | 45.6 |
| 2 | 2 | 11 600 | 1.19 | 30.2 |
| 3 | 4 | 15 900 | 1.19 | 49.6 |
| 4 | 16 | 28 000 | 1.21 | 91.9 |

[a]Multimodal molecular weight distribution

Example 62

Preparation of Low Polydispersity Poly(vinyl Benzoate) using 2-cyanoprop-2-yl Dithiobenzoate (15)

Stock solution (I) was prepared by dissolving 2,2'-azobis (2-methylpropane) (10 mg) in vinyl benzoate (10 mL). Stock solution (II) was prepared by dissolving 2-cyanoprop-2-yl dithiobenzoate (15) (160 mg) in vinyl benzoate (10 mL). A mixture comprising stock solution (I) (0.14 mL), stock solution (II) (2.75 ml) and vinyl benzoate (3 g) was added to an ampoule. The ampoule was degassed, sealed and heated at 150° C. for 48 hours. The resultant viscous liquid was reduced in vacuo to poly(vinyl benzoate). $M_n$ 3 490, $M_w$ 4 500, $M_w/M_n$ 1.29, 25% conversion.

Example 63

Preparation of Low Polydispersity Poly(vinyl Butyrate) Using 2-cyanopropyl Dithiobenzoate (15)

Stock solution (I) was prepared by dissolving 2,2'-azobis (2-methylpropane) (10 mg) in vinyl butyrate (10 mL). A mixture comprising of stock solution (I) (0.14 mL), 2-cyanoprop-2-yl dithiobenzoate (15) (50 mg) and vinyl butyrate (5.9 g) was added to an ampoule. The ampoule was degassed, sealed and heated at 150° C. for 48 hours. The resultant viscous liquid was reduced in vacuo to poly(vinyl butyrate). $M_n$ 1 051, $M_w$ 1 326, $M_w/M_n$ 1.26, 5% conversion.

Example 64

Preparation of Low Polydispersity Poly(p-styrenesulfonic Acid Sodium Salt) Using Sodium Salt of 4-cyano-4-(thiobenzoylthio)pentanoic Acid A stock solution of 4,4'-azobis(4-cyanopentanoic acid) (23.4 mg) and p-styrenesulfonic acid sodium salt (4.99 g) in distilled water (25 mL) was prepared. An aliquot of the stock solution (10 mL) was transferred to a conical flask containing sodium salt of 4-cyano-4-(thiobenzoylthio)pentanoic acid (50 mg). This solution was divided into two equal parts and transferred to two ampoules. A control experiment was carried out by placing an aliquot (5 mL) of the stock solution to another ampoule. The ampoules were degassed, sealed and heated at 70° C. for the periods of time indicated in Table 31 below.

TABLE 31

Molecular weight and conversion data for poly(p-styrenesulfonic acid sodium salt) prepared with 4-cyano-4-(thiobenzoylthio)pentanoic acid at 70° C. in aqueous solution

| Entry | time/hr | $M_n$[a] | $M_w/M_n$ | % Conv.[b] |
|---|---|---|---|---|
| 1 (control) | 1 | 73 000 | 2.27 | 96.0 |
| 2 | 4 | 8 000 | 1.13 | 73.4 |
| 3 | 14.25 | 10 500 | 1.20 | 84.1 |

[a]GPC molecular weight in polystyrene sulfonic acid sodium salt standard equivalents. Operation conditions: columns, Waters' Ultrahydrogel 500, 250 and 120; eluent, 0.1 M sodium nitrate/acetontrile (80:20); flow rate, 0.8 mL/min.; detector, Waters 410 RI; injection size, 0.25 mg/50 mL.
[b]% Conversion was estimated by $^1$H-nmr.

The following example illustrates narrow polydispersity cyclopolymer synthesis.

Example 65

Preparation of Low Polydispersity Cyclopolymer of 2,4,4,6-tetrakis(ethoxycarbonyl)-1,6-heptadiene Using 2-phenylprop-2-yl Dithiobenzoate (5)

A mixture of 2,4,4,6-tetrakis(ethoxycarbonyl)-1,6-heptadiene (1.05 g), 2-phenylprop-2-yl dithiobenzoate (5) (24.5 mg), azobisisobutyronitrile (4.5 mg) and o-xylene (3 mL) were added to an ampoule degassed and sealed. The ampoule was heated at 60° C. for 64 hours. After removal of all the volatiles, the cyclopolymer was isolated (0.70 g, 66.7% conversion) with Mn 6540, Mw 8920, and polydispersity 1.36. In the absence of dithiobenzoate (5), the corresponding cyclopolymer was isolated (88% conversion) with $M_n$ 23 400, $M_w$ 47 200, and $M_w/M_n$ 2.01.

The following two examples demonstrate the preparation of copolymers.

Example 66

Preparation of Low Polydispersity Poly(methyl Methacrylate-co-styrene) in the Presence of 2-phenylprop-2-yl Dithiobenzoate (5)

A series of copolymerizations of styrene/methyl methacrylate (52:48 mole ratio) in the presence of 2-phenylprop-2-yl dithiobenzoate (5) was carried out. The experimental conditions were similar to those described by O'Driscoll and Huang [*Eur. Polym. J.*, 25(7/8), 629, (1989); ibid, 26(6), 643, (1990)]. Aliquots (5 mL) of styrene/methyl methacrylate (52:48 mole ratio) were transferred to eight ampoules containing dimethyl 2,2'-azobisisobutyrate (11.5 mg) four of which contained phenylprop-2-yl dithiobenzoate (5) (76.4 mg). The ampoules were degassed, sealed and placed in a constant temperature bath at 60° C. After the specified time (see Table), the polymerizations were quenched by cooling the ampoule in cold water and the polymer was isolated by removal of all the volatiles. Results are summarized in Table 32 below.

TABLE 32

Molecular weight and conversion data for poly(methyl methacrylate-co-styrene) prepared with 2-phenylprop-2-yl dithiobenzoate (5) at 60° C.

| Entry | time/hr | parameter | control (no CTA) | with CTA (5) |
|---|---|---|---|---|
| 1 | 5 | $M_n$ | 123 200 | 10 100 |
|   |   | $M_W/M_n$ | 1.67 | 1.21 |
|   |   | % Conv. | 16.8 | 9.9 |
| 2 | 10 | $M_n$ | 125 900 | 20 200 |
|   |   | $M_W/M_n$ | 1.75 | 1.17 |
|   |   | % Conv. | 32.2 | 22.8 |
| 3 | 15 | $M_n$ | 148 800 | 26 900 |
|   |   | $M_W/M_n$ | 1.82 | 1.22 |
|   |   | % Conv. | 46.9 | 34.2 |
| 4 | 20 | $M_n$ | 257 000 | 33 800 |
|   |   | $M_W/M_n$ | 2.39 | 1.21 |
|   |   | % Conv. | 91.2 | 43.1 |

Example 67

Preparation of Low Polydispersity Poly(acrylonitrile-co-styrene) in the Presence of 2-phenylprop-2-yl Dithiobenzoate (5)

A stock solution consisting of styrene (7.27 g) and acrylonitrile (2.27 g) was prepared. An aliquot (2 g) of the stock solution was reserved for the control experiment and 2-phenylprop-2-yl dithiobenzoate (5) (28.5 mg) was added to the remaining stock solution. Aliquots of this solution (2 g) were transferred to ampoules which were degassed, sealed and heated at 100° C. for the times indicated in Table 33 below.

TABLE 33

Molecular weight and conversion data for poly(acrylonitrile-co-styrene) prepared with 2-phenylprop-2-yl dithiobenzoate(5) at 100° C.

| Entry | time/hr | $M_n$ | $M_w/M_n$ | % Conv. |
|---|---|---|---|---|
| 1 (control) | 18 | 424 000 | 1.70 | 96.0 |
| 2 | 4 | 20 100 | 1.04 | 26.0 |
| 3 | 8 | 33 000 | 1.05 | 42.0 |
| 4 | 18 | 51 400 | 1.07 | 70.7 |

The following example illustrates synthesis of a quaternary copolymer.

Example 68

Preparation of Low Polydispersity Quaternary Copolymers of MMA/iBMA/HEMA/Styrene in the Presence of 2-phenylprop-2-yl Dithiobenzoate A stock solution was prepared comprising methyl methacrylate (1.5 g), isobutyl methacrylate (3.38 g), hydroxyethyl methacrylate (1.5 g), styrene (1.13 g), 2-butanone (2 g), azobisisobutyronitrile (0.05 g) and 2-phenylprop-2-yl dithiobenzoate (5) (0.163 g). Aliquots (4.5 g) of the stock solution were placed into ampoules which were degassed, sealed and heated at 60° C. for 1 and 24 hours. The quaternary copolymer was isolated by evaporation and characterized by GPC analysis. Results are summarized in Table 34 below.

TABLE 34

Molecular weight and conversion data for poly(hydroxethyl methacrylate-co-isobutyl methacrylate-co-methyl methacrylate-co-styrene) prepared with 2-phenylprop-2-yl dithiobenzoate (5) at 60° C.

| Entry | time/hr | $M_n$ | $M_w/M_n$ | % Conversion |
|---|---|---|---|---|
| 1 | 1 | 633 | 1.23 | — |
| 2 | 24 | 11 300 | 1.47 | >99 |

Example 69

Preparation of Low Polydispersity Styrene-butadiene Polymers using 1-phenylethyl Dithiobenzoate (4)

This example was carried out to demonstrate that it is possible to prepare low polydispersity styrene/butadiene (SBR, 30:70) copolymers with 1-phenylethyl dithiobenzoate (4) as chain transfer agent.

A mixture of styrene (36 g), water (197.6 g), potassium rosin soap (6.26 g), sodium formaldehyde sulfoxylate (0.060 g), tri-potassium phosphate (0.293 g), sodium carbonate (0.036 g), potassium persulfate (0.366 g) and chain transfer agent (1-phenylethyl dithiobenzoate (4) (0.09 g) or tert-dodecyl mercaptan (0.191 g)) was placed in a 7 oz glass bottle containing crown seal with nitrite gaskets. The bottle was degassed by purging with nitrogen, and then added butadiene (84 g). The polymerization was carried out at 50° C. and after 8 hours, SBR copolymers were obtained having $M_w/M_n$ of 1.17 when dithioester (4) was used as the chain transfer agent, and $M_w/M_n$ 2.08 when tert-dodecyl mercaptan was used as chain transfer agent. Some retardation is observed with respect to the control polymerization.

Example 70

Preparation of Low Polydispersity Block Copolymers of Methyl Methacrylate and Methacrylic Acid in the Presence of 2-phenylprop-2yl Dithiobenzoate To a reaction vessel, azobisisobutyronitrile (10 mg) and a poly(methyl methacrylate) sample (1 g, made with the use of 2-phenylprop-2-yl dithiobenzoate (5) ($M_n$ 3231, $M_w/M_n$ 1.17), see Example 51) were dissolved in N,N-dimethylformamide (4.1 mL) and added to methacrylic acid (0.8 g). The ampoule was degassed, sealed and heated at 60° C. for 16 hours. After removal of solvent, poly(methyl methacrylate-block-methacrylic acid) was obtained (near quantitative conversion). GPC results obtained after methylation of the diblock, gave polymer of $M_n$ 4718 and $M_w/M_n$ 1.18.

The following two examples illustrate the synthesis of triblock copolymers from a bifunctional chain transfer agent. In the first step, a linear polymer with thiobenzoylthio groups at each end is prepared. The second step provides an ABA triblock.

Example 71

Preparation of Poly(styrene-block-methyl methacrylate-block-styrene) in the Presence of 1,4-bis(2-thiobenzoylthioprop-2-yl)benzene (10)

Step 1: Preparation of Low Polydispersity Poly(methyl methacrylate) with a Dithioester Group at Each End A stock solution (I) of azobisisobutyronitrile (20.26 mg) and methyl methacrylate (15 mL) in benzene (5 mL) was prepared. An aliquot of stock solution (I) (2 mL) was transferred to an ampoule and was used as a control experiment. 1,4-Bis(2-thiobenzoylthioprop-2-yl)benzene (10) (93.64 mg) was added to the remaining stock solution (I) to form stock solution (II). Aliquots (4 mL) of the stock solution (II) were transferred into ampoules which were degassed, sealed and heated at 60° C. for the times indicated. The results are summarized in Table 35 below.

TABLE 35

Molecular weight and conversion data for poly(methyl methacrylate) prepared with 1,4-bis(2-thiobenzoylthioprop-2-yl)benzene (10) at 60° C.

| Entry | time/hr | $M_n$ | $M_w/M_n$ | % Conv. |
|---|---|---|---|---|
| 1 | 2 | 5 400 | 1.32 | 9.8 |
| 2 | 4 | 12 200 | 1.22 | 23.3 |
| 3 | 8 | 23 600 | 1.18 | 49.9 |
| 4 | 16 | 45 800 | 1.15 | 98.5 |

Step 2: Preparation of Poly(styrene-block-methyl methacrylate-block-styrene)

The 8 hour poly(methyl methacrylate) sample (1.55 g, $M_n$ 23 600, $M_w/M_n$ 1.18) was dissolved in ethyl acetate and transferred to an ampoule. The solvent was removed under reduced pressure and azobisisobutyronitrile (3.1 mg) and styrene (10 mL) were added. The resulting solution was degassed, sealed and heated at 60° C. for 20 hours. After removal of all the volatiles, the title block copolymer (orange pink colour foam) was isolated (3.91 g, 26% conversion), $M_n$ 59 300, $M_w/M_n$ 1.76 (trimodal).

Example 72

Preparation of Poly(hydroxyethyl methacrylate-block-methyl methacrylate-block-hydroxyethyl methacrylate) in the Presence of 1,4-bis(2-thiobenzoylthioprop-2-yl)benzene (10)

Step 1: Preparation of Low Polydispersity Poly(methyl methacrylate) with a Dithioester Group at Each End Stock solution (I) consisting of azobisisobutyronitrile (20 mg) and methyl methacrylate (15 mL) in benzene (5 mL) was prepared. This solution (18 mL) was transferred to an ampoule containing 1,4-bis(2-thiobenzoylthioprop-2-yl)benzene (10) (93.5 mg) which was then degassed, sealed and heated at 60° C. for 8 hours. The poly(methyl methacrylate) obtained (4.7 g, 33.5% conversion) had $M_n$ 23 000 and $M_w/M_n$ 1.16.

Step 2: Preparation of Narrow Polydispersity Poly(hydroxyethyl methacrylate-block-methyl methacrylate-block-hydroxyethyl methacrylate)

A solution of poly(methyl methacrylate) (1.74 g, $M_n$ 23 000, $M_w/M_n$ 1.16) in tetrahydrofuran (14 mL), hydroxyethyl methacrylate (1 mL) and azobisisobutyronitrile (10 mg) were transferred to an ampoule which was then degassed, sealed and heated at 60° C. for 4 hours. The product poly(hydroxyethyl methacrylate-block-methyl methacrylate-block-hydroxyethyl methacrylate) (40.2% conversion) had $M_n$ 28 500 and $M_w/M_n$ 1.18.

The following example illustrates the synthesis of star block copolymers with a soft inner core (n-butyl acrylate) and hard outer shell (styrene).

Example 73

Preparation of Star Block Copolymers of n-butyl Acrylate and Styrene using 1,2,4,5-tetrakis(thiobenzoylthiomethyl)benzene (9)

Step 1: Star Polymers of n-Butyl Acrylate

Stock solution (I) of 2,2'-Azobis(2,4,4-trimethylpentane) (VR-110) (8 mg) in benzene (25 mL) and stock solution (11) of 1,2,4,5-tetrakis(thiobenzoylthiomethyl)benzene (9) (75 mg) in benzene (10 mL) were prepared. n-Butyl acrylate (4 mL), stock solution (I) (3 mL) and stock solution (II) (3 mL) were transferred to an ampoule which was degassed, sealed and heated at 110° C. for 67 hours to give star poly(n-butyl acrylate) (39.4% conversion), $M_n$ 23 250, $M_w/M_n$ 2.22.

Step 2: Star Block Copolymers of n-Butyl Acrylate and Styrene

The star poly(n-butyl acrylate) (0.5 g, $M_n$ 23248, $M_w/M_n$ 2.22) and styrene (2 mL) were transferred into an ampoule degassed, sealed and heated at 110° C. for 16 hours. After removal of all the volatiles, the star block copolymer was obtained (1.3 g, 71.4% conversion) with $M_n$ 82 500 and $M_w/M_n$ 2.16.

The following example demonstrates the synthesis of a graft copolymer based on the use of a polymer chain with pendant dithioester groups.

Example 74

Preparation of Graft Copolymers in the Presence of 3- & 4-vinylbenzyl Dithiobenzoates (19)

Step 1: Poly(methyl methacrylate-co-vinylbenzyl dithiobenzoate)

A solution of vinylbenzyl dithiobenzoate (19) (100 mg, mixture of meta and para isomers), azobisisobutyronitrile (15 mg), methyl methacrylate (10 mL) in 2-butanone (10 mL) was placed in an ampoule, degassed, sealed and heated at 60° C. for 6 hours to give poly(methyl methacrylate-co-vinylbenzyl dithiobenzoate) (3.52 g, 37.6% conversion). GPC: $M_n$ 102 000, $M_w/M_n$ 2.26. $^1$H-nmr analysis indicates an average of 3.5 thiobenzoylthio groups per polymer chain.

Step 2: Poly(methyl methacrylate-graft-styrene)

A degassed solution of the poly(methyl methacrylate-co-vinylbenzyl dithiobenzoate) from step 1 (0.5 g) and azobisisobutyronitrile (1.0 mg) in freshly distilled styrene (5.0 mL) was heated at 60° C. for 40 hours. The polymerization gave a red gel which was insoluble in THF, acetone and chloroform. The finding that polystyrene homopolymer could not be extracted from the mixture indicates the success of the grafting experiment.

Example 75

Preparation of Low Polydispersity Poly(methyl methacrylate) by Emulsion Polymerization at 80° C. in the Presence of 2-phenylprop-2-yl Dithiobenzoate (5)

A 5-necked reaction vessel fitted with a condenser, thermocouple, and mechanical stirrer was charged with water (14.8 g), sodium dodecyl sulfate (3.0 g of 10% aqueous solution) and 2-phenylprop-2-yl dithiobenzoate (5) (0.325 g) and the mixture degassed under nitrogen at 90° C. for 50 minutes. Feeds of methyl methacrylate (37.5 mL, 0.316 mL/min) and 4,4'-azobis(4-cyanopentanoic acid) (900 mg) in water (85 g, 0.312 mL/min) were then commenced. After 65 min the concentration of the initiator feed was halved [4,4'-azobis(4-cyanopentanoic acid) (450 mg) in water (94 g, 0.312 mL/min)]. On completion of the feeds, the reaction was held at 90° C. for a further 90 minutes. The reaction mixture was sampled periodically to provide samples for GPC analysis (see Table 36 below).

TABLE 36

Molecular weight and conversion data for poly(methyl methacrylate) prepared with 2-phenylprop-2-yl dithiobenzoate (5) at 90° C. in emulsion

| Entry | MMA added (mL) | $M_n$ | $M_w$ | $M_w/M_n$ | % Conv |
|---|---|---|---|---|---|
| 1 | 20.5 | 3 550 | 4 530 | 1.27 | 14.2 |
| 2 | 37.5 | 12 000 | 15 800 | 1.32 | 41.4 |
| 3 | final | 26 000 | 34 900 | 1.33 | 89.8 |

The following three examples demonstrate the 'one-pot' synthesis of block copolymers by sequential monomer addition.

Example 76

Preparation of Poly(methyl methacrylate-block-styrene) by Emulsion Polymerization at 80° C. in the Presence of 2-phenylprop-2-yl Dithiobenzoate (5)

A 5-necked reaction vessel fitted with a condenser, thermocouple, and mechanical stirrer was charged with water (37.5 g) and sodium dodecyl sulfate (3 g of 10% aqueous solution). The mixture was degassed at 80° C. under nitrogen for 40 minutes and a solution of 4,4'-azobis(4-cyanopentanoic acid) (71 mg) and 2-phenylprop-2-yl dithiobenzoate (5) (18.1 mg) in methyl methacrylate (1.6 g) was added as a single shot. Further 2-phenylprop-2-yl dithiobenzoate (5) (108 mg) in methyl methacrylate (2.5 g) was then added over 10 minutes. A feed of methyl methacrylate (15 g) was commenced at a rate of 0.188 mL/min by syringe pump. This was followed immediately by a feed of styrene (24 mL) at a rate of 0.2 mL/min. Further initiator (31.5 mg) was added every 90 minutes during the feed periods. The reaction was held at 80° C. for a further 120 minutes. The reaction mixture was sampled periodically to provide samples for GPC analysis (see Table 37 below).

TABLE 37

Molecular weight and conversion data for poly(methyl methacrylate) and poly(methyl methacrylate-block-styrene) prepared with 2-phenylprop-2-yl dithiobenzoate (5) at 80° C. in emulsion

| Entry | Sample | $M_n$ | $M_w$ | $M_w/M_n$ | % Conv | $M_n$ (calc) |
|---|---|---|---|---|---|---|
| 1 | +7.5 g MMA | 9 350 | 11 430 | 1.22 | 43 | 9 430 |
| 2 | +15 g MMA | 25 000 | 38 600 | 1.54 | 85 | 31 022 |
| 3 | +6 mL styrene | 36 000 | 61 000 | 1.68 | >99 | 46 790 |
| 4 | +12 mL styrene | 49 000 | 92 000 | 1.86 | >99 | 57 171 |
| 5 | +18 mL styrene | 52 000 | 107 000 | 2.06 | >99 | 67 552 |
| 6 | +24 mL styrene | 72 000 | 162 000 | 2.24 | >99 | 77 553 |
| 7 | Final | 72 000 | 159 000 | 2.21 | >99 | 77 553 |

The use of GPC equipped with both a diode array detector and a refractive index detector provides evidence of block formation and purity. Polymers with dithiobenzoate end groups have a strong absorption in the region 300-330 nm (exact position depends on solvent and substituents). Neither polystyrene nor poly(methyl methacrylate) have significant absorption at this wavelength.

Example 77

Preparation of Low Polydispersity Diblock Poly(butyl methacrylate-block-Styrene) via Emulsion Polymerisation at 80° C. in the Presence of 2-phenylprop-2-yl Dithiobenzoate (5)

Water (52 g) and sodium dodecyl sulfate (0.55 g of 10% aqueous solution) were charged to 5-neck, 250 mL reactor fitted with a stirrer, condenser and thermocouple and degassed under nitrogen at 80° C. for 40 minutes. A solution of 4,4'-azobis(4-cyanopentanoic acid) (71 mg) and 2-phenylprop-2-yl dithiobenzoate (5) (17 mg) in butyl methacrylate (1.7 g) was added as a single shot. Further 2-phenylprop-2-yl dithiobenzoate (5) (71 mg) in butyl methacrylate (2.7 g) was then added over 10 minutes. Feeds of butyl methacrylate (16 g, 0.2485 mL/min) was then added by syringe pump. Further portions of 4,4'-azobis(4-cyanopentanoic acid) were added at 82 minutes (35 mg) and on completion of the monomer feed at 142 minutes (20 mg). Feeds of styrene (15 g, 0.2 mL/min) and 4,4'-azobis(4-cyanopentanoic acid) in water (38.7 g, 0.472 mL/min) were then commenced. On completion of the feeds the reaction mixture was held at 80° C. for a further 90 minutes. The reaction mixture was sampled periodically for GPC analysis.

TABLE 38

Molecular weight and conversion data for poly(butyl methacrylate) and poly(butyl methacrylate-block-styrene) prepared with phenylprop-2-yl dithiobenzoate (5) at 80° C. in emulsion

| Entry | Sample | $M_n$ | $M_w$ | $M_w/M_n$ | % Conv | $M_n$ (calc) |
|---|---|---|---|---|---|---|
| 1 | +10.9 mL BMA | 26 000 | 39 000 | 1.50 | 54 | 22 585 |
| 2 | +16.01 g BMA | 63 000 | 77 000 | 1.22 | 95 | 57 742 |
| 3 | final | 65 500 | 81 000 | 1.23 | >99 | 60 876 |
| 4 | +11.4 mL Styrene | 70 500 | 115 000 | 1.63 | 84 | 91 846 |
| 5 | +15 g Styrene | 78 000 | 136 000 | 1.74 | 84 | 98 579 |
| 6 | Reaction Final | 103 000 | 177 000 | 1.73 | >99 | 105 710 |

Example 78

Preparation of Low Polydispersity Poly(styrene-block-methyl methacrylate) by Emulsion Polymerization in the Presence of Benzyl Dithioacetate (12)

Water (50 g) and sodium dodecyl sulfate (3 g of 10% aqueous solution) were charged to a 5-neck reaction vessel equipped with a condenser, thermocouple, and mechanical stirrer. The mixture was heated at 80° C. for 40 minutes while purging with nitrogen. A solution of 4,4'-azobis(4-cyanopentanoic acid) (87.5 mg) and benzyl dithioacetate (12) (104.2 mg) in styrene (2.3 g) was then added as a single shot. Feeds of styrene (13.6 g, 0.2 mL/min) and an initiator solution (4,4'-azobis(4-cyanopentanoic acid) (531 mg, 0.089 mL/min) in water (100 g)) were commenced. On completion of the feeds the reaction temperature was increased to 90° C. and the addition of feeds of methyl methacrylate (15 mL, 0.316 mL/min) and 4,4'-azobis(4-cyanopentanoic acid) (265 mg) in water (100 g) (0.312 mL/min) was commenced. After completion of the feeds the reaction was held at 90° C. for a further 60 minutes. The reaction mixture was sampled periodically for GPC analysis.

TABLE 39

Molecular weight and conversion data for poly(styrene) and poly(methyl methacrylate-block-styrene) prepared with benzyl dithioacetate in emulsion

| Entry | Sample | $M_n$ | $M_w$ | $M_w/M_n$ | % Conv | $M_n$ (calc) |
|---|---|---|---|---|---|---|
| 1 | +6 mL styrene | 7 690 | 10 500 | 1.37 | 43 | 4 560 |
| 2 | +12 mL styrene | 22 000 | 29 000 | 1.33 | 89 | 1 824 |
| 3 | +15 mL styrene | 24 000 | 32 000 | 1.35 | >99 | 25 480 |
| 4 | +7.5 mL MMA | 35 000 | 49 000 | 1.41 | 92 | 36 390 |
| 5 | +15 mL MMA | 39 000 | 61 000 | 1.56 | 84 | 45 513 |
| 6 | Final | 41 000 | 65 000 | 1.57 | 87 | 47 620 |

The following two examples demonstrate the synthesis of narrow polydispersity polymers by solution polymerization including a monomer feed.

Example 79

Preparation of Low Polydispersity Poly(n-butyl acrylate) by the Solution Feed Polymerization of Butyl Acrylate at 60° C. in the Presence of 1-phenylethyl Dithiobenzoate (4)

n-Butyl acrylate (10 g), ethyl acetate (10 g), azobisisobutyronitrile (50 mg) and 1-phenylethyl dithiobenzoate (4) were placed in a 100 mL 3-neck round bottom flask equipped with a condenser, mechanical stirrer and thermocouple, and degassed with nitrogen over 40 minutes with stirring. The flask was then placed in a pre-heated water bath at 60° C. After 60 minutes a solution of n-butyl acrylate (10 g) in ethyl acetate (5 g) was added over 3 hours (0.088 mL/min) by syringe pump. On completion of the feed the reaction was held at 60° C. for a further 120 minutes. The reaction mixture was sampled periodically for GPC analysis.

TABLE 40

Molecular weight and conversion data for poly(n-butyl acrylate) prepared with 1-phenylethyl dithiobenzoate (4) at 60° C. in ethyl acetate

| Entry | time/min | $M_n$ | $M_w$ | $M_w/M_n$ | % Conv | $M_n$ (calc) |
|---|---|---|---|---|---|---|
| 1 | 60 | 3 500 | 3 900 | 1.10 | 6.7 | 2 431 |
| 2 | 120 | 6 300 | 6 900 | 1.09 | 13.5 | 6 471 |
| 3 | 180 | 9 600 | 10 900 | 1.13 | 19.3 | 11 578 |
| 4 | 240 | 14 600 | 16 900 | 1.15 | 22.9 | 16 514 |
| 5 | 300 | 18 800 | 23 000 | 1.20 | 34.6 | 24 955 |
| 6 | 300 | 21 700 | 25 800 | 1.19 | 45.0 | 32 410 |

Example 80

Preparation of Low Polydispersity Poly(methyl methacrylate) by the Solution Feed Polymerization of Methyl Methacrylate at 80° C. in the Presence of 2-phenylprop-2-yl Dithiobenzoate (5).

Methyl methacrylate (15 mL), 2-butanone (5 mL), azobisisobutyronitrile (20 mg) and 2-phenylprop-2-yl dithiobenzoate (5) (0.53 g) were placed in a 250 mL multi-neck round bottom flask equipped with a condenser, mechanical stirrer and thermocouple, and degassed with nitrogen over 40 minutes with stirring. The mixture was then placed in a pre heated water bath at 80° C. A solution of azobisisobutyronitrile (26.7 mg) in methyl methacrylate (40 mL) and 2-butanone (13.3 mL) was then added over 4 hours (0.222 mL/min). On completion of the feed the reaction was held at 80° C., for a further 90 minutes. The reaction mixture was sampled periodically for GPC analysis.

TABLE 41

Molecular weight and conversion data for poly(methyl methacrylate) prepared with 2-phenylprop-2-yl dithiobenzoate (5) at 60° C. in 2-butanone

| Entry | time/min | $M_n$ | $M_w$ | $M_w/M_n$ | % Conv | $M_n$ (calc) |
|---|---|---|---|---|---|---|
| 1 | 60 | 1 280 | 1 550 | 1.20 | 12.9 | 1 549 |
| 2 | 120 | 1 860 | 2 340 | 1.26 | 12.4 | 2 085 |
| 3 | 180 | 2 900 | 3 730 | 1.28 | 23.5 | 5 074 |

TABLE 41-continued

Molecular weight and conversion data for poly(methyl methacrylate) prepared with 2-phenylprop-2-yl dithiobenzoate (5) at 60° C. in 2-butanone

| Entry | time/min | $M_n$ | $M_w$ | $M_w/M_n$ | % Conv | $M_n$ (calc) |
|---|---|---|---|---|---|---|
| 4 | 240 | 4 100 | 5 200 | 1.27 | 32.0 | 8 445 |
| 5 | final | 5 400 | 6 800 | 1.26 | 29.7 | 7 838 |

The following example demonstrates the effectiveness of dithioesters in providing living characteristics in the suspension polymerization of methyl methacrylate. In order to achieve a low polydispersity the molecular weight must substantially smaller than the control molecular weight.

Example 81

Suspension Polymerization of Methyl Methacrylate in the Presence of 2-phenylprop-2-yl Dithiobenzoate This example illustrates a suspension polymerization with VAZO® 64 initiator and an ACRYLSOL® A1 polyacrylic acid suspension agent. The molecular weight of the product is controlled with 2-phenylprop-2-yl dithiobenzoate (5). The components employed are as follows where 2-phenylprop-2-yl dithiobenzoate (5) is used at 0.10 by weight of monomer:

| | Parts by Weight |
|---|---|
| Part 1 | |
| Deionized water | 1490.39 |
| ACRYLSOL ® A1 | 49.68 |
| Subtotal | 1540.07 |
| Part 2 | |
| methyl methacrylate | 451.13 |
| 2-phenylprop-2-yl dithiobenzoate | 0.45 |
| Subtotal | 451.58 |
| Part 3 | |
| VAZO ® 64 | 3.10 |
| Deionized water | 3.10 |
| Subtotal | 6.20 |
| Final Total | 1997.85 |

The initiator VAZO® 64 is commercially available from DuPont (Wilmington, Del.) and ACRYLSOL® A is commercially available from Rohm & Haas (Philadelphia, Pa.). Into a jacketed flask with internal baffles and a high speed stirrer is added methyl methacrylate monomer, a low molecular weight polyacrylic acid, and deionized water. The multi-bladed stirrer is engaged and increased in speed to about 800 rpm. The contents of the flask are heated to 65° C. and the initiator is added. The contents are heated to 80° C. and maintained at that temperature for two hours. The contents of the flask are filtered through cloth and washed with deionized water. The solid polymer is placed in an oven to dry. The reaction product obtained is 451.13 parts (23.41%) solids, the remainder being deionized water solvent.

TABLE 42

Molecular weight data for poly(methyl methacrylate) prepared with 2-phenylprop-2-yl dithiobenzoate (5) by suspension polymerization

| Entry | 2-phenylprop-2-yl dithiobenzoate (5) wt % | $M_n$ | $M_n/M_w$ |
|---|---|---|---|
| 1 | 0 | 82 000 | 3.75 |
| 2 | 0.10 | 52 000 | 2.01 |
| 3 | 0.50 | 26 500 | 2.13 |
| 4 | 1.00 | 16 200 | 1.31 |
| 5 | 0 | 82 800 | 3.70 |
| 6 | 0 | 9 300 | 3.76 |
| 7 | 1.00 | 14 900 | 1.52 |
| 8 | 1.00 | 15 500 | 1.30 |
| 9 | 2.00 | 9 150 | 1.24 |
| 10 | 2.00 | 9 490 | 1.30 |

Example 82

Polymerization of n-butyl Acrylate in the Presence of High Concentrations of 2-phenylprop-2-yl Dithiobenzoate (5)

A stock solution of 1,1'-azobis(1-cyclohexanecarbonitrile) (15 mg) in n-butyl acrylate (30 g) and 2-butanone (30 g) was prepared. Aliquots (5 mL) were placed in each of four ampoules and the required amounts of stock solution of the dithioester (20 mg) in 2-butanone (0.55 mL) were added to give the concentrations indicated in Table 43. The samples were degassed, sealed and heated at 80° C. for 60 minutes. The polymer formed was isolated by evaporation and characterized by GPC.

TABLE 43

Molecular weight and conversion data for poly(n-butyl acrylate) prepared with 2-phenylprop-2-yl dithiobenzoate (5) at 80° C. in 2-butanone

| Entry | Dithioester | [CTA] × $10^{-3}$ M | $M_n$ | $M_w/M_n$ | Conv % |
|---|---|---|---|---|---|
| 1 | (5) | 0.74 | 67 000 | 1.84 | 40.2 |
| 2 | (5) | 1.54 | 52 000 | 1.56 | 38.4 |
| 3 | (5) | 2.94 | 30 000 | 1.26 | 25.0 |
| 4 | none | 0 | 86 000 | 2.45 | 51.6 |

The following two examples illustrate the effect of the nature of the dithioester on the extent of retardation observed when using high concentrations of dithioester. The results demonstrate that the extent of retardation can be minimized by selecting a particular dithioester according to the monomer being polymerized on the basis of the considerations discussed in the text.

Example 83

Polymerization of Styrene with Various Dithioesters

A stock solution of 1,1'-azobis(1-cyclohexanecarbonitrile) (15 mg) in styrene (15 g) and toluene (15 g) was prepared. Aliquots (5 mL) were placed in each of four ampoules and the required amounts of a stock solution of the appropriate dithioesters were added to give the concentrations indicated in Table 44. The samples were degassed, sealed and heated at 110° C. for the times indicated in Table 44. The polymer formed was isolated by evaporation and characterized by GPC.

TABLE 44

Molecular weight and conversion data for polystyrene prepared with various dithioesters at 110° C. in toluene

| Entry | CTA | time (min) | $M_n$ | $M_w/M_n$ | Conv % | [CTA] × $10^{-2}$ M |
|---|---|---|---|---|---|---|
| 1 | 2-cyanoprop-2-yl dithiobenzoate (15) | 60 | 2 330 | 1.08 | 15.4 | 2.2 |
| 2 | 2-cyanoprop-2-yl dithiobenzoate (15) | 120 | 4 100 | 1.07 | 27.2 | 2.2 |
| 3 | 2-phenylprop-2-yl dithiobenzoate (5) | 60 | 2 010 | 1.07 | 1.40 | 1.8 |
| 4 | 2-phenylprop-2-yl dithiobenzoate (5) | 120 | 3 250 | 1.07 | 16.9 | 1.8 |
| 5 | none | 60 | 62 000 | 1.57 | 21.3 | 0 |
| 6 | none | 120 | 68 000 | 1.62 | 28.2 | 0 |

Example 84

Polymerizations of n-butyl Acrylate with Various Dithioesters

A stock solution of dimethyl 2,2'-azobisisobutyrate (7.5 mg) in n-butyl acrylate (15 g) and 2-butanone (15 g) was prepared. Aliquots (5 mL) were placed in each of four ampoules and the required amounts of a stock solution of the dithioester were added to give the concentrations indicated in Table 45. The samples were degassed, sealed and heated at 80° C. for the times indicated in Table 45. The polymer formed was isolated by evaporation and characterized by GPC.

TABLE 45

Molecular weight and conversion data for poly(n-butyl acrylate) prepared with various dithioesters at 80° C. in in 2-butanone

| Entry | CTA | time (min) | $M_n$ | $M_w/M_n$ | Conv % | [CTA] × $10^{-2}$ M |
|---|---|---|---|---|---|---|
| 1 | 2-phenylprop-2-yl dithiobenzoate (5) | 60 | 275 | 1.11 | 2.1 | 2.4 |
| 2 | 2-phenylprop-2-yl dithiobenzoate (5) | 120 | 555 | 1.20 | 3.6 | 2.4 |
| 3 | benzyl dithiobenzoate (3) | 60 | 790 | 1.16 | 3.2 | 2.6 |
| 4 | benzyl dithiobenzoate (3) | 120 | 1 397 | 1.21 | 7.3 | 2.6 |
| 5 | benzyl dithioacetate (12) | 60 | 3 550 | 1.18 | 25.1 | 3.4 |
| 6 | benzyl dithioacetate (12) | 120 | 6 100 | 1.17 | 49.8 | 3.4 |
| 7 | none | 60 | 76 000 | 2.63 | 67.8 | 0 |
| 8 | none | 120 | 89 000 | 2.34 | 80.8 | 0 |

The following two Examples demonstrate the use of the invention in mini-emulsion polymerization.

Example 85

Preparation of Low Polydispersity Polystyrene via Mini-emulsion Polymerization with Benzyl Dithiobenzoate (3) at 70° C.

A 5-neck reaction vessel fitted with a stirrer, condenser and thermocouple was charged with water (75 g) and sodium dodecyl sulfate (215.2 mg), cetyl alcohol (53 mg), sodium bicarbonate (16.7 mg). The mixture was then homogenized for 10 minutes. Styrene (18.84 g) was added and the mixture homogenized for a further 5 minutes. The reaction mixture was stirred (300 rpm) for 40 minutes while the temperature was raised to 70° C. Benzyl dithiobenzoate (3) (107 mg) and 2,2'-azobis(2-cyano-2-butane) (40.7 mg) were then added. The reaction mixture was heated at 70° C. with stirring (300 rpm) for 6 hours and sampled periodically for GPC analysis.

TABLE 46

Molecular weight and conversion data for polystyrene prepared with benzyl dithiobenzoate (3) in mini-emulsion at 70° C.

| Entry | time/min | $M_n$ | $M_w/M_n$ | % Conversion |
|---|---|---|---|---|
| 1 | 60 | 2 080 | 1.78 | 7 |
| 2 | 120 | 2 980 | 1.21 | 11 |
| 3 | 180 | 4 450 | 1.11 | 14 |
| 4 | 360 | 6 470 | 1.23 | 33 |

A control experiment (no dithioester) gave $M_n$ 480 000, $M_w/M_n$ 2.4, conversion 99% after 360 minutes.

Example 86

Preparation of Low Polydispersity Polystyrene by Mini-emulsion Polymerization with Benzyl Dithiobenzoate (3) at 70° C.

An experiment carried out under conditions similar to those used for Example 85 but with potassium persulfate as initiator gave polystyrene $M_n$ 6 770, $M_w/M_n$ 1.15, conversion 26% after 360 minutes.

Example 87

Preparation of Low Polydispersity Poly(ethylene Oxide-block Styrene)

A mixture of styrene (2.25 g) and dithioester (28) (0.14 g) was placed in an ampoule which was then degassed, sealed and heated at 110° C. for 5.5 hours. The excess styrene was evaporated to give the title block copolymer with $M_n$ 11 700 and $M_w/M_n$ 1.4 at 27% conversion. Examination of the product by Gel permeation chromatography coupled with UV-Visible spectrophotometry established the presence of the dithiobenzoate end group in the final block copolymer.

Example 88

Preparation of Low Polydispersity Poly(ethylene Oxide-block Styrene)

A mixture of styrene (4.5 g) and dithioester (29) (0.5 g) was placed in an ampoule which was then degassed, sealed and heated at 110° C. for 21 hours. The excess styrene was evaporated to give the title block copolymer with $M_n$ 7 800 and $M_w/M_n$ 1.07 at 40% conversion.

What is claimed is:

1. A process for the synthesis of polymers selected from the group consisting of:

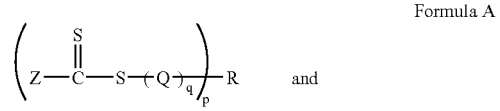

Formula A

-continued

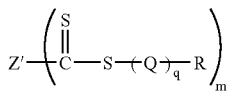

Formula B comprising contacting:

(i) one or more monomers selected from the group consisting of vinyl monomers of structure $CH_2=CUV$, maleic anhydride, N-alkylmaleimide, N-arylmaleimide, dialkyl fumarate and cyclopolymerizable monomers;

(ii) a thiocarbonylthio compound selected from the group consisting of:

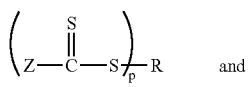 and

Formula C

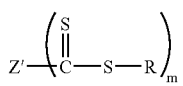

Formula D having a chain transfer constant greater than about 0.1; and (iii) free radicals produced from a free radical source; and controlling the polydispersity of the polymer being formed by varying the ratio of the number of molecules of (ii) to the number of molecules of (iii);

the polymer of Formula A being made by contacting (i), (ii) C and (iii) and the polymer of Formula B being made by contacting (i), (ii) D and (iii);

wherein:

Z is selected from the group consisting of hydrogen, chlorine, optionally substituted alkyl, optionally substituted aryl, optionally substituted heterocyclyl, optionally substituted alkylthio, optionally substituted alkoxycarbonyl, optionally substituted aryloxycarbonyl (—COOR"), carboxy (—COOH), optionally substituted acyloxy (—$O_2CR$"), optionally substituted carbamoyl (—CONR"$_2$), cyano (—CN), dialkyl- or diaryl-phosphonato [—P(=O)(OR")$_2$], dialkyl- or diaryl-phosphonato [—P(=O)R"$_2$], and a polymer chain formed by any mechanism;

Z' is a m-valent moiety derived from a member of the group consisting of optionally substituted alkyl, optionally substituted aryl and a polymer chain; where the connecting moieties are selected from the group that consists of aliphatic carbon, aromatic carbon, and sulfur;

Q is selected from the group consisting of repeating unit

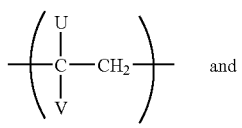 and repeating units from maleic anhydride, N-alkylmaleimide, N-arylmaleimide, dialkyl fumarate and cyclopolymerizable monomers;

U is selected from the group consisting of hydrogen, halogen, optionally substituted $C_1$-$C_4$ alkyl wherein the substituents are independently selected from the group that consists of hydroxy, alkoxy, aryloxy (OR"), carboxy, acyloxy, aryloxy ($O_2CR$"), alkoxycarbonyl and aryloxy-carbonyl ($CO_2R$");

V is selected from the group consisting of hydrogen, R", $CO_2H$, $CO_2R$", COR", CN, $CONH_2$, CONHR", CONR"$_2$, $O_2CR$", OR" and halogen;

R is selected from the group consisting of optionally substituted alkyl; an optionally substituted saturated, unsaturated or aromatic carbocyclic or heterocyclic ring; optionally substituted alkylthio; optionally substituted alkoxy; optionally substituted dialkylamino; an organometallic species; and a polymer chain prepared by any polymerization mechanism; in compounds C and D, R· is a free-radical leaving group that initiates free radical polymerization;

R" is selected from the group consisting of optionally substituted $C_1$-$C_{18}$ alkyl, $C_2$-$C_{18}$ alkenyl, aryl, heterocyclyl, aralkyl, alkaryl wherein the substituents are independently selected from the group that consists of epoxy, hydroxy, alkaxy, acyl, acyloxy, carboxy and carboxylates, sulfonic acid and sulfonates, alkoxy- or aryloxy-carbonyl, isocyanato, cyano, sily, halo, and dialkylamino;

q is 1 or an integer greater than 1;

p is 1 or an integer greater than 1; when p≧2 then R=R';

m is an integer ≧2; and

R' is a p-valent moiety selected from a member of the group consisting of optionally substituted alkyl, optionally substituted aryl and a polymer chain; where the connecting moieties are selected from the group consisting of aliphatic carbon, aromatic carbon, silicon, and sulfur; in compounds C, R· is a free radical leaving group that initiates free radical polymerization.

2. The process according to claim 1 comprising controlling polydispersity by varying the ratio of the number of molecules of (ii) to (iii) as follows:

(a) lower polydispersity by increasing the ratio of (ii) to (iii); and (b) increase polydispersity by decreasing the ratio of (ii) to (iii).

3. The process according to claim 2 comprising increasing the ratio of (ii) to (iii) and obtaining a polymer having a polydispersity below about 1.5.

4. The process according to claim 1 comprising selecting the following monomer repeating unit:

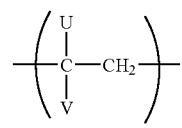

from (i).

5. The process according to claim 1 comprising selecting the monomer units Q and the value of q so that when q≧1 and Q results from a single monomer species, then the polymer is homopolymer when q≧2 end Q results from the selection from 2 or more different monomer species in irregular sequence then the polymer is copolymer; and when q≧2 and Q results from the selection from 2 or more different monomer species in which each different monomer or group of monomers appears in a discrete sequence then the polymer is block copolymer.

6. The process according to claim 1 wherein the thiocarbonylthio compound is selected from the group consisting of:

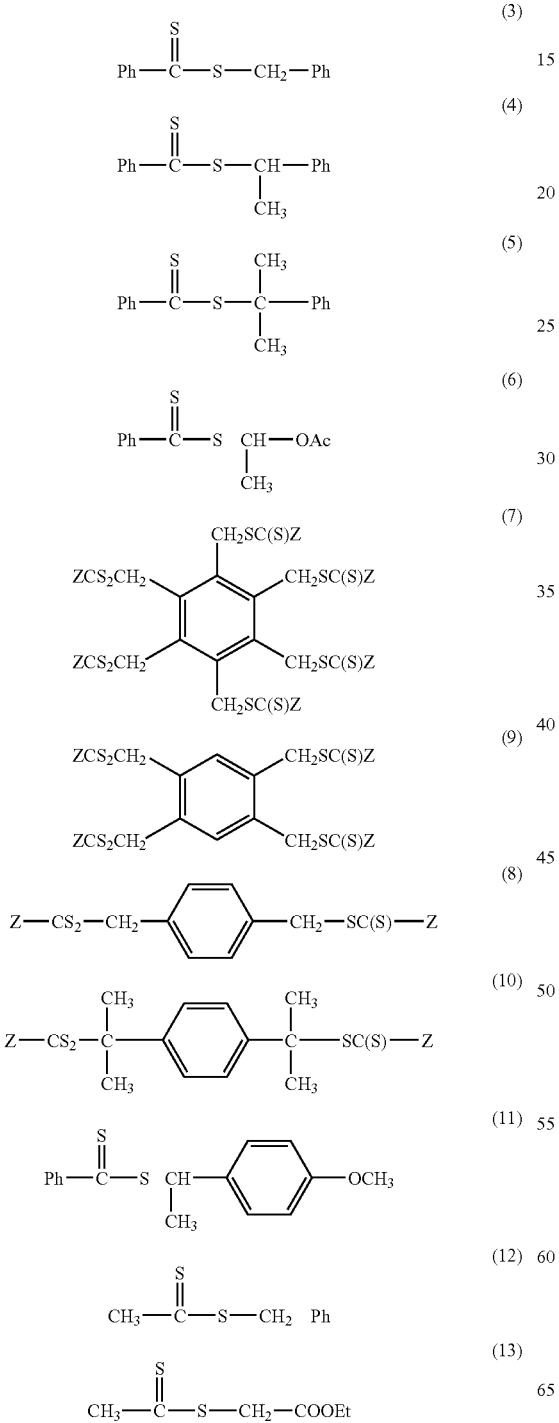

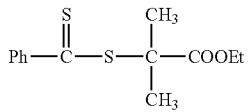

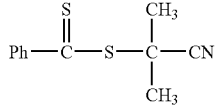

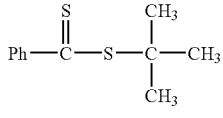

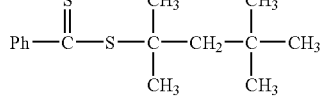

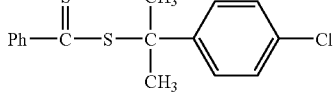

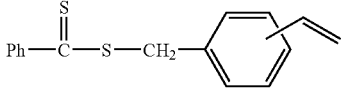

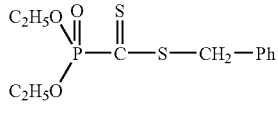

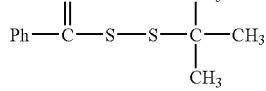

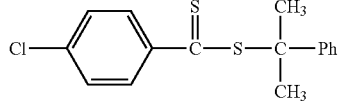

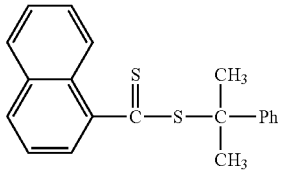

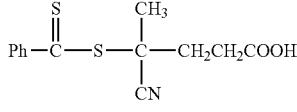

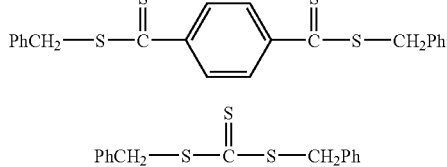

-continued

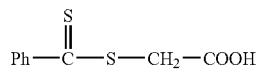
(27)

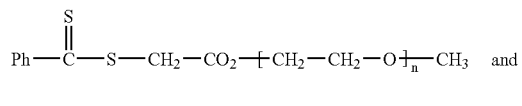 and
(28)

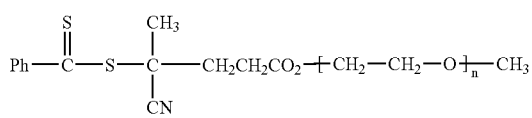
(29)

wherein Z is phenyl.

7. The process of claim 1 wherein said polymer chain comprises condensation polymers or chain polymers.

8. The process of claim 7 wherein said condensation polymers comprise polyesters, polycarbonates, poly(alkylene oxide)s, nylons or polyurethanes.

9. The process of claim 8 wherein said polyesters comprise polycaprolactones or polyethylene terephthalates.

10. The process of claim 7 wherein said chain polymers comprise poly(meth)acrylates or polystyrenics.

11. The process of claim 1 wherein said copolymerizable monomers comprise compounds containing two or more unsaturated links suitably disposed to allow propagation by a sequence of intramolecular and intermolecular additions steps that lead to incorporation of cyclic units in polymer backbone.

12. The process of claim 11 wherein said copolymerizable monomers comprise 1,6-dienes, substituted 1,6-heptadienes or monomers of the generic structure:

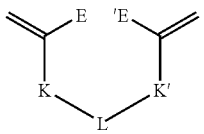

wherein E and E' are independently selected from the group consisting of H, $CH_3$, CN, COOAlkyl and Ph; K and K' are selected from the group consisting of $CH_2$, C=O, $Si(CH_3)$ and O; L is selected from the group consisting of $C(E)_2$, O, $N(Alkyl)_2$ salts, and $P(O)Alkyl$; and where K, K', L, E and E' are chosen such that said monomer undergoes cyclopolymerization.

13. The process of claim 1 wherein said vinyl monomers comprise acrylate and methacrylate esters, acrylic and methacrylic acids, styrenes, acrylamides, methacrylamides, methacrylonitriles, and mixtures thereof.

14. The process of claim 13 wherein said vinyl monomers further comprise mixtures with other monomers.

15. The process of claim 1, 13 or 14 wherein said vinyl monomers comprise methyl methacrylate, ethyl methacrylate, propyl methacrylate or isomers thereof, butyl methacrylate and isomers thereof, 2-ethyihexyl methacrylate, isobomyl methecrytate, methecrylic acid, benzyl methacrylate, phenyl methacrylate, methacrylonitrile, alpha-methylstyrene, methyl ecrylate, ethyl acrylate, propyl acrylate or isomers thereof, butyl acrylate or Isomers thereof, 2-ethylhexyl acrylate, Isobornyl acrylate, acrylic acid, beflzyl acrylate, phenyl acrylate, acrylonitrile, styrene, functional methacrylates, acrylates and styrenes selected from glycidyl methacrylate, 2-hydroxyathyl methacrylate, hydroxypropyl methacrylate or isomers thereof, hydroxybutyl methacrylate or isomers thereof, N,N-dimethylaminoethyl methacrylate, N,N-diethylaminoethyl methacrylate, triethyleneglycol acid, glycidyl acrylate, 2-hydroxyathyl acrylate, hydroxypropyl acryiste and isomers thereof, hydroxybutyl acrylate and isomers thereof, N,N-dimethylaminoethyl acrylate, N,N-diethylaminoethyl acrylate, tristhyleneglycol acrylate, methacrylamide, N-methylacrylamlde, N,N-dimethytacrylamlde, N-tert-butylmethacrylamide, N-n-butylmethacrylamide, N-methylolmethacryfamide, N-ethylolmethacrylamide, N-tert-butylacrylamlde, N-n-butylacrylamide, N-methylolacrylamide, N-ethylolacrylamide, vinyl benzoic acid and isome thereof, diethylaminostyrene and isomers thereot alpha-methylvinyl benzoic acid and isomers thereof, diethylamino alpha-methylstyrene and isomers thereof, p-vinylbenzene sulfonic acid, p-vinylbenzene sulfonic sodium salt, trimethoxysilyipropyl methacrylate, triethoxysilylpropyl methacrylate, tributoxysilylpropyl methacrylate, dimethoxymethylsilylproyl methacrylate, diethoxymethyl-silylpropylmethacryrate, dibutoxmethylsilylpropyl methacrylate, diisopropoxymethytsilylpropyl methacrylate, dimethoxysilylpropyl methacrylate, diethoxysilylpropyl methacrylate, dibutoxysilyipropyl methacrylate, diisopropoxysilylpropyl methacrylate, trimethoxysilylpropyl acrylate, triethoxysilylpropyl acrylate, tributoxysilylpropyl acrylate, dimethoxymethylsilylpropyl acrylate, diethoxymethylsilylpropyl acrylate, dibutoxmethylsilylpropyl acrylate, diisopropoxymethytsilylpropyl acrylate, dimethoxysilylpropyl acrylate, diethoxysilylpropyl acrylate, dibutoxysilyipropyl acrylate, diisopropoxysilylpropyl acrylate, vinyl acetate, vinyl butyrate, vinyl benzoate, vinyl chloride, vinyl fluoride, vinyl bromide, maleic anhydride, N-phenylmaleimide, N-butyimaleimide, N-vinylpyrrolidone, N-vinylcarbazole, butadiene, isoprene, chloroprene, ethylene, or propylene.

16. The process of claim 1 wherein substituents for R, R', Z, Z', U and V comprise epoxy, hydroxy, alkoxy, acyl, acyloxy, carboxy and carboxylates, sulfonic acid and sulfonates, alkylcarbonyloxy, isocyanato, cyano, silyl, halo or dialkylamino.

17. The process of claim 1 wherein substituents for R, R', Z, Z', U and V comprise alkoxy, alkyl or aryl.

18. The process of claim 1 wherein said heterocyclic ring comprises a ring structure containing 3 to 10 atoms at least one of which is selected from O, N and S.

19. The process of claim 1 wherein said polymer of the formula A or formula B is a end-functional polymer, block polymer, multiblock polymer, gradient polymer, star polymer, graft polymer or a branched polymer.

20. The process of claim 1 wherein said free radical source comprises thermal initiators, spontaneous generation from monomers, redox initiating systems, photochemical initiating systems or high energy radiation.

21. The process of claim 20 wherein said thermal initiator comprises 2,2'-azobis(isobutyronitrile), 2,2'-azobis(2-cyano-2-butane), 4,4'-azobis(4-cyanopentanoic acid), 1,1'-azobis(cyclohexanecarbonitrile), dibenzoyl peroxide, or ammonium peroxydisulfate.

22. The process of claim 1, wherein said process is carried out at temperatures in the range of −20° C. to 200° C.

23. The process of claim 1 wherein said process is carried out in emulsion, solution or suspension.

24. The process of claim 23 wherein said process is carried out in a batch, semi-batch, continuous or feed mode.

25. The process of claim 1, 20, 21. 22, 23 or 24 wherein said thiocarbonyithic compound is added before polymerization is commenced.

26. The process of claim 1, 20, 21, 22, 23 or 24 wherein polydispersity of said polymer of formula A or B is controlled by adding said thiocarbonylthio compound over the course of polymerization.

27. The process of claim 1, 20, 21, 22, 23 or 24 wherein said polymer of formula A or B having multimodal molecular weight distribution can be produced by adding said thiocarbonylthio compound over the course of polymerization.

28. The process of claim 1 wherein said process is carried out in emulsion or suspension.

29. The process of claim 28 wherein a reaction medium is water.

30. The process of claim 1 wherein said process is carried out in a feed mode.

31. The process of claim 30 wherein said process comprises:
(i) charging a reactor with a medium and said thiocarbonylthio compound in a reactor; and
(ii) heating and stirring contents in said reactor while introducing in said reactor said monomers in said medium and said free radical source dissolved or suspended in said medium.

32. The process of claim 30 wherein said process comprises:
(i) charging a reactor with a medium and said thiocarbonylthio compound and a portion of said monomers in a reactor; and
(ii) heating and stirring contents in said reactor while introducing in said reactor a remaining portion of said monomers in said medium and said free radical source dissolved or suspended in said medium.

33. The process of claim 31 or 32 further comprising continuing heating of contents In said reactor for additional period after completing feeding of said free radical source and said monomers.

34. The process of claim 33 further comprising isolating said polymers of the formula A or B by stripping off said medium and unreacted said monomers.

35. The process of claim 1 wherein Z in said Formula C is a substituted alkylthio.

36. The process of claim 1 or 35 wherein R in said Formula C is a substituted alkylthio.

37. The process of claim 1 or 35 wherein R in said Formula C is a substituted alkyl.

38. The process of claim 37 wherein R in said Formula C is —C(Me)$_2$C$_6$H$_4$Cl, —C(Me)$_2$Ph, —C(Me)$_2$COOEt, —C(Me)$_2$CN, —C(Me)(CH$_2$CH$_2$COOH)CN, or —C(Me)(CH$_2$CH$_2$COONa)CN.

39. The process of claim 1 or 35 wherein R in said Formula C is a substituted alkylthio substituted with cyano.

40. The process of claim 1 or 36 wherein R in said Formula C is a substituted alkyl substituted with cyano.

41. The process of claim 35 wherein substituent in said substituted alkylthio is phenyl.

42. The process of claim 35 wherein said substituted alkylthio is benzylthio.

43. The process of claim 42 wherein R is benzyl.

44. The process of claim 1 wherein said thiocarbonylthio compound is 4-cyanopentanoic acid dithiobenzoate or is sodium salt.

45. The process of claim 44 wherein medium is water.

* * * * *